United States Patent
Perez et al.

(10) Patent No.: US 12,252,517 B2
(45) Date of Patent: Mar. 18, 2025

(54) HOOK FUSION PROTEIN FOR REGULATING THE CELLULAR TRAFFICKING OF A TARGET PROTEIN

(71) Applicants: INSTITUT CURIE, Paris (FR); CENTRE NATIONAL DE LA RECHERCHE SCIENTIFIQUE (CNRS), Paris (FR)

(72) Inventors: Franck Perez, Paris (FR); Zelia Gouveia, L'hay les Roses (FR); Gaelle Boncompain, Chatillon (FR)

(73) Assignees: INSTITUT CURIE, Paris (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 18/464,507

(22) Filed: Sep. 11, 2023

(65) Prior Publication Data

US 2024/0018197 A1 Jan. 18, 2024

Related U.S. Application Data

(63) Continuation of application No. 16/757,410, filed as application No. PCT/EP2018/078930 on Oct. 22, 2018, now abandoned.

(30) Foreign Application Priority Data

Oct. 20, 2017 (EP) .................... 17306453

(51) Int. Cl.
| | |
|---|---|
| C07K 14/725 | (2006.01) |
| A61K 39/00 | (2006.01) |
| C07K 14/36 | (2006.01) |
| C07K 14/705 | (2006.01) |
| C07K 14/74 | (2006.01) |
| C12N 15/63 | (2006.01) |

(52) U.S. Cl.
CPC .......... *C07K 14/36* (2013.01); *A61K 39/0011* (2013.01); *C07K 14/7051* (2013.01); *C07K 14/70539* (2013.01); *C07K 14/7056* (2013.01); *C12N 15/63* (2013.01); *A61K 2039/5156* (2013.01); *A61K 2039/5158* (2013.01); *C07K 2319/04* (2013.01); *C07K 2319/10* (2013.01)

(58) Field of Classification Search
CPC ................ C07K 14/36; C07K 14/7051; C07K 14/70539; C07K 14/7056; C07K 2319/04; C07K 2319/10; C12N 15/63
See application file for complete search history.

(56) References Cited

U.S. PATENT DOCUMENTS

| 5,672,691 A | 9/1997 | Kopetzki et al. |
| 7,265,205 B2 | 9/2007 | Wu et al. |
| 9,353,161 B2 | 5/2016 | Wong et al. |

FOREIGN PATENT DOCUMENTS

| WO | 2010142785 A1 | 12/2010 |
| WO | 2013038272 A2 | 3/2013 |
| WO | 2016012623 A1 | 1/2016 |

OTHER PUBLICATIONS

Boncompain, G., et al. "Synchronization of Secretory Protein Traffic in Populations of Cells", Nature Methods, vol. 9, No. 5, May 2012, pp. 493-498.
Bonifacino, J., et al. "Signals for Sorting of Transmembrane Proteins to Endosomes and Lysosomes", Annual Review of Biochemistry, vol. 72, No. 1, Mar. 6, 2003, pp. 395-447.
Szymczak, A., et al. "Development of 2A Peptide-Based Strategies in the Design of Multicistronic Vectors", Expert Opinion on Biological Therapy (2005), vol. 5, No. 5, pp. 627-638.
Ercan, E., et al. "Di-Arginine Signals and the K-Rich Domain Retain the Ca2+ Sensor STIM1 in the Endoplasmic Reticulum", Traffic 2012, vol. 13, No. 7, Apr. 25, 2012, pp. 992-1003.
Barrette-Ng et al. "The structure of the SBP-Tag-streptavidin complex reveals a novel helical scaffold bridging binding pockets on separate subunits". Acta Crystallogr D Biol Crystallogr. 2013; 69(Pt 5):879-887.
Brown et al. "A mammalian protein targeted by G1-arresting rapamycin-receptor complex". Nature. 1994; 369 (6483):756-758.
Bulbarelli et al. "Trafficking of tail-anchored proteins: transport from the endoplasmic reticulum to the plasma membrane and sorting between surface domains in polarised epithelial cells". J Cell Sci. 2002; 115(Pt 8): 1689-1702.
Carrasco et al. "An endoplasmic reticulum retention function for the cytoplasmic tail of the human pre-T cell receptor (TCR) alpha chain: potential role in the regulation of cell surface pre-TCR expression levels". J Exp Med.2001; 193(9):1045-1057.
Clackson. "Controlling mammalian gene expression with small molecules". Curr Opin Chem Biol. 1997; 1(2):210-218.

(Continued)

*Primary Examiner* — Julie Ha
*Assistant Examiner* — Kristina M Hellman
(74) *Attorney, Agent, or Firm* — Maier & Maier, PLLC

(57) ABSTRACT

A hook fusion protein, which includes a hook domain and at least one cytoplasmic carboxyl endoplasmic reticulum (ER) retention signal and/or at least one cytoplasmic amino terminal endoplasmic reticulum (ER) retention signal; wherein the hook fusion protein is a soluble protein that localizes in the cytoplasm. Also, a nucleic acid system for intracellular targeting control including a nucleic acid encoding a target fusion protein including a hook fusion protein, and a nucleic acid encoding a target fusion protein including a hook-binding domain; wherein the target fusion protein is a membrane protein; and wherein the hook fusion protein localizes in the ER when bound to the target fusion protein. Additionally, a vector system, viral particle system, host cell and kit include these nucleic acids. Further, the vector system, viral particle system, host cell or kit for use as a medicament, in particular for immunotherapy.

9 Claims, 6 Drawing Sheets

Figure 1:
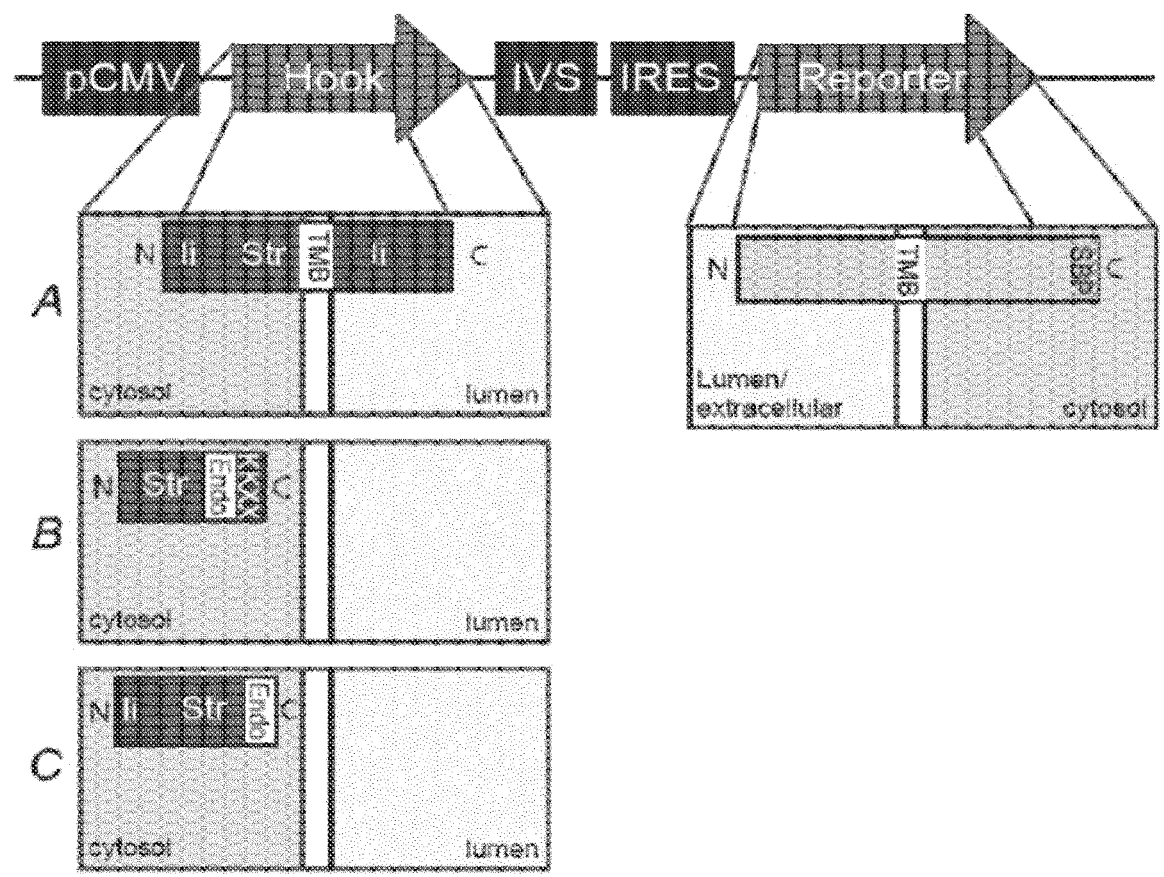

Specification includes a Sequence Listing.

(56) References Cited

OTHER PUBLICATIONS

Fu et al. "Localization of ribophorin II to the endoplasmic reticulum involves both its transmembrane and cytoplasmic domains". Eur J Cell Biol. 2000; 79(4):219-228.

Jones et al. "Lentiviral vector design for optimal T cell receptor gene expression in the transduction of peripheral blood lymphocytes and tumor-infiltrating lymphocytes". Hum Gene Ther. 2009; 20(6):630-640.

Kim et al. "High cleavage efficiency of a 2A peptide derived from porcine teschovirus-1 in human cell lines, zebrafish and mice". PLoS One. 2011; 6(4):e18556; 8 pages.

Letourneur et al. "Coatomer is essential for retrieval of dilysine-tagged proteins to the endoplasmic reticulum". Cell. 1994; 79(7):1199-1207.

Maki et al. "Complementary DNA encoding the human T-cell FK506-binding protein, a peptidylprolyl cis-trans isomerase distinct from cyclophilin". Proc Natl Acad Sci U SA. 1990; 87(14):5440-5443.

Parmar et al. "Polybasic trafficking signal mediates golgi export, ER retention or ER export and retrieval based on membrane-proximity". PLoS One. 2014; 9(4):e94194; 10 pages.

Schutze et al. "An N-terminal double-arginine motif maintains type II membrane proteins in the endoplasmic reticulum". EMBO J. 1994; 13(7):1696-1705.

Standaert et al. "Molecular cloning and overexpression of the human FK506-binding protein FKBP". Nature. 1990; 346(6285):671-674.

Strub In et al. "The complete sequence of the mRNA for the HLA-DR-associated invariant chain reveals a polypeptide with an unusual transmembrane polarity". EMBO J. 1984; 3(4):869-872.

Strub In et al. "Two forms of the Ia antigen-associated invariant chain result from alternative initiations at two in-phase AU Gs". Cell. 1986; 47(4):619-625.

Siymczak et al. "Correction of multi-gene deficiency in vivo using a single 'self-cleaving' 2A peptide-based retroviral vector". Nat Biotechnol. 2004;22(5):589-594.

Tach Ibana et al. "Improving the solubility of artificial ligands of streptavidin to enable more practical reversible switching of protein localization in cells". Chembiochem. 2017; 18(4):358-362.

Tan et al. "Coexpression of double or triple copies of the rabies virus glycoprotein gene using a 'self-cleaving' 2A peptide-based replication-defective human adenovirus serotype 5 vector". Biologicals. 2010; 38(5):586-593.

Terai et al. "Artificial Ligands of Streptavidin (ALiS): discovery, characterization, and application for reversible control of intracellular protein transport". J Am Chem Soc. 2015;137(33): 10464-10467.

Traub et al. "Cargo recognition in clathrin-mediated endocytosis". Cold Spring Harb Perspect Biol. 2013; 5(11): a016790; 23 pages.

Wang et al. "2A self-cleaving peptide-based multi-gene expression system in the silkworm *Bombyx mori*". Sci Rep. 2015;5: 16273; 1 O pages.

Wells et al. "Reaching for high-hanging fruit in drug discovery at protein-protein interfaces". Nature. 2007; 450(7172):1001-1009.

Wu et al. "Engineering soluble monomeric streptavidin with reversible biotin binding capability". J Biol Chem. 2005; 280(24):23225-23231.

Wu et al. "Structure-guided design of an engineered streptavidin with reusability to purify streptavidin-binding peptide tagged proteins or biotinylated proteins". PLoS One. 2013;8(7):e69530; 10 pages.

Yen et al. "Biological activity of ovine IL-23 expressed using a foot-and-mouth disease virus 2A self-cleaving peptide". Cytokine. 2013; 61 (3):744-746.

Abraham et al., "Control of protein trafficking by reversible masking of transport signals," Mol. Biol. Cell 27:1310-1391 (epublished Mar. 3, 2016) (Year: 2016).

Wilson et al., "The use of mRNA display to select high-affinity protein-binding peptides," PNAS 98: 3750-3755 (2001) (Year: 2001).

Drumm et al, Genetic Variation and Clinical Heterogeneity in Cystic Fibrosis, Annu. Rev. Pathol. Mech. Dis., 2012, 7, pp. 267-282 (Year: 2012).

Yampolsky et al, The Exchangeability of Amino Acids in Proteins, Genetics, 2005, 170, pp. 1459-1472 (Year: 2005).

HOOK FUSION PROTEIN FOR REGULATING THE CELLULAR TRAFFICKING OF A TARGET PROTEIN

CROSS-REFERENCE TO RELATED APPLICATIONS

This application is a continuation of U.S. application Ser. No. 16/757,410, filed Apr. 19, 2020, which is national stage entry under 35 U.S.C. § 371 of PCT/EP2018/078930, filed Oct. 22, 2018, which itself claims priority to EP Patent Application Number 17306453.6, filed Oct. 20, 2017; the contents of each of which is incorporated by reference herein in its entirety.

REFERENCE TO SEQUENCE LISTING

The Sequence Listing submitted herewith via EFS-Web is hereby incorporated by reference in its entirety. The name of the file is Y.Ref. 12470325COA-O.Ref. IBIO-1606-US-2-Election Restriction-ICOSA Amended sequence listing.xml, the size of the file is 40,071 bytes, and the date of creation of the file is Jun. 12, 2024.

INTRODUCTION

The inventors of the present application have previously described a molecular system named RUSH (Retention Using Selective Hooks) capable of controlling the intracellular trafficking of a target fusion protein and in particular that can be used to control the targeting of a target protein in a given cellular compartment.

RUSH was described as a two state system based on the reversible interaction of a hook protein fused to streptavidin and stably anchored in the donor compartment with a target fusion protein fused to a streptavidin-binding peptide (SBP), which is therefore immobilized in said donor compartment. Addition of biotin caused a synchronous release of the target protein from the hook which is therefore free to resume its journey to its final compartment.

The RUSH has been successfully applied to Chimeric Antigen Receptors (CARs) as a tool to selectively control the expression of the CARs at the cell surface, to prevent adverse effects (see WO2016/012623).

The various hooks that have been described contained a mutant of a stromal interaction molecule 1 (STIM1-NN, a type I protein) that localizes in the endoplasmic reticulum (ER), an isoform of the human invariant chain of the major histocompatibility complex (Ii, a type II protein) that has an N-terminal arginine-based motif being an ER retention signal; or a C-terminal ER retention signal (KDEL (SEQ ID NO: 27)). However these hooks had some limitations.

In particular, it remains of high relevance to develop hooks, which have the smallest size as possible. Indeed, it is known that vector production, notably lentivirus production, is inversely proportional to the size of the protein of interest. Consequently higher size inserts, such as the ones containing the hook and the reporter (above 4 kb) impaired the production of lentivirus required for the transduction and/or generation of stable cell lines, namely modified immune cells containing CAR.

Also, vector constructs are based on cellular mRNAs translation through initiation at internal ribosome entry sites (IRES s) to generate a bicistronic or multicistronic vector containing the hook and the reporter. It has been reported that transduction of the proteins through IRES can impair their expression (Jones, Peng et al. 2009). Moreover, the large size of the IRES sequence and differences in gene expression levels before and after IRES are other limiting factors. New strategies have been envisioned to overcome such limitation, such as the use of self-cleaving 2A peptide (2A) or 2A peptides (Jones, Peng et al. 2009). 2A peptides allow simultaneous translation of the protein upstream and downstream of the 2A peptide (Szymczak, Workman et al. 2004, Tan, Liang et al. 2010, Yen and Scheerlinck 2013, Wang, Wang et al. 2015). However, while extremely powerful, 2A peptides impose that a few amino acids be added at the extremity of the 5' and 3' ORF which prevent the use of carboxy-terminal signals ER retention signals, like -KDEL (SEQ ID NO: 27) or -K(X)KXX (SEQ ID NO: 30), that cannot be extended to stay active.

Furthermore, the previously described hooks are expressed in the endoplasmic reticulum (ER) (i.e.: anchored in the ER membrane or expressed in the ER lumen). Therefore such hooks do not support a fully reversible system, wherein the target membrane protein could be retrieved from the membrane. Similarly such hooks do not allow preventing the target membrane protein to leak out from the ER, and in particular the leaking of the target membrane protein to the cell membrane.

Lastly, the hooks that were stably anchored in the membrane from the ER can only retain in the ER proteins that are in their close vicinity.

The present invention provides an innovative technical solution which overcomes the limitations as previously mentioned.

SUMMARY OF THE INVENTION

The inventors have surprisingly discovered that the carboxy-terminal KKXX (SEQ ID NO: 4) (or K(X)KXX (SEQ ID NO: 30)) sequence ER retention signal that is described in the art as working in "Cis", when present on membrane proteins, is able to work in "trans" when present on a soluble cytosolic protein, if said protein is recruited on a membrane protein. Indeed, their results now show that a soluble cytosolic protein bearing an ER retention signal is stably expressed in the cytosol but is targeted in the endoplasmic reticulum when bound to a membrane protein. They also showed that this interaction can be rendered reversible, such that retention in the ER can also be reversible.

Therefore the present invention relates to a hook fusion protein comprising
  a hook domain
  at least one cytoplasmic carboxy terminal endoplasmic reticulum (ER) retention signal and/or at least one cytoplasmic amino terminal endoplasmic reticulum (ER) retention signal;
  wherein the hook fusion protein is a soluble protein that localizes in the cytoplasm.

Such soluble hooks support a fully reversible control of the membrane expression of a membrane target protein. The hooks of the present invention should also allow retrieving proteins that leaked out from the ER as these new "trans" hooks can sample the full cytosol and retrieve protein from the Golgi back to the ER and potentially from later compartments.

The inventors have further shown that a targeting sequence based on the invariable chain Ii of human major histocompatibility complex (MHC), corresponding to the first 46 amino acids of the N terminal portion, can also be used as an ER retention signal when fused in the N-terminal part of a soluble hook of the invention. The results of the present application also show for the first time that such a short fragment of the invariable chain Ii of the MHC can be used as a retention signal.

"Trans" hooks of the invention having such an N terminal ER retention signal are also highly advantageous as they can be included in a vector upstream of a 2A peptide, as their C terminal is now free to accommodate the 2A peptide without compromising the function of the hook.

Advantageously also such "trans" hooks according to the invention are of much smaller size than the hooks that have been previously described.

Lastly, as also further shown in the results, an endocytosis signal such as copied from the LAMP1 protein can be further fused to the hook protein to create a hook that can therefore induce trans-signaling for endocytosis and ER retrograde transport and retention in a reversible way. Such a hook should therefore solve the problem of target proteins leaking from the ER down to the plasma membrane.

Thus, the hook fusion protein of the inventions comprises a hook domain (or a hook core) that is typically a streptavidin sequence.

The carboxy terminal endoplasmic reticulum (ER) retention signal of the hook fusion protein of the invention can be K(X)KXX (SEQ ID NO: 30), and/or the amino terminal endoplasmic reticulum (ER) retention signal can be a fragment of the isoform of the human invariant chain of the major histocompatibility complex protein Ii as herein defined.

The hook fusion protein of the invention preferably comprises an endocytosis signal, preferably consisting of YXXI (SEQ ID NO: 28).

The invention also includes a nucleic acid comprising a nucleic acid sequence encoding the hook fusion protein as herein defined.

The nucleic acid of the invention can further comprise a nucleic acid sequence encoding a target fusion protein comprising a hook-binding domain, wherein said target fusion protein is a chimeric antigen receptor comprising:
 a binding domain;
 a hook-binding domain, and
 at least one activation domain;
or alternatively comprising:
 the full NKG2D or a functional variant thereof,
 at least one activation domain, and
 a hook-binding domain The invention also includes a nucleic acid system for intracellular targeting control comprising
 (a) a nucleic acid encoding a hook fusion protein as herein defined, and
 (b) a nucleic acid encoding a target fusion protein comprising a hook-binding domain;
 wherein said target fusion protein in a membrane protein; and
 wherein the hook fusion protein localizes in the ER when bound to the target fusion protein; optionally
 wherein the hook fusion protein comprises a streptavidin domain and the target fusion protein comprises a streptavidin-binding domain, optionally
 wherein the target fusion protein is a chimeric antigen receptor as herein defined.

The present invention also includes a vector system comprising one or more vectors comprising
 (a) the nucleic acid sequence as herein defined, and optionally
 (b) a nucleic acid encoding a target fusion protein comprising a hook-binding domain;
 wherein the nucleic acids (a) and (b) are located on the same or on different vectors; optionally
 wherein the hook fusion protein comprises a streptavidin domain and the target fusion protein comprises a streptavidin-binding domain.

In a vector system of the invention, the nucleic acids (a) and (b) can be located on the same vector, wherein the nucleic acid (a) is inserted upstream of an IRES sequence and the nucleic acid (b) is inserted downstream of said IRES sequence.

In a vector system of the invention, the nucleic acids (a) and (b) can be located on the same vector wherein:
 i) the nucleic acid (a) comprises an Ii retention signal in its N terminal sequence and is inserted upstream of a 2A peptide sequence, or
 ii) the nucleic acid (a) comprises a K(X)KXX (SEQ ID NO: 30) retention signal in its C terminal sequence and is inserted downstream of a 2A peptide sequence.

In one embodiment the vector system of the invention comprises the nucleic acid sequence (b)
 wherein said nucleic acid sequence (b) comprises a streptavidin-binding domain, and
 wherein said nucleic acid sequence (b) is inserted downstream of the 2A peptide in the i) configuration or upstream of the 2A peptide in the ii) configuration.

Typically in a vector system according to the invention, the target fusion protein encoded by the nucleic acid (b) is a chimeric antigen receptor as herein defined The present invention also includes a viral particle system comprising a vector system as herein defined; optionally wherein the viral particle is a lentiviral particle.

The present invention also includes an isolated cell comprising a vector system or a viral particle system as herein defined.

The present invention also relates to an in vitro method for regulating the intracellular trafficking in a host cell of a target protein;
 wherein said target protein is a fusion protein comprising a hook binding domain; and
 wherein the method comprises expressing in said host cell a vector system or a viral particle system as herein defined; wherein the hook fusion protein and the target fusion protein are capable of conditional interaction in the absence of a ligand for the hook core domain, optionally wherein the hook core domain is streptavidin, the hook-binding domain is a streptavidin-binding domain and the ligand is biotin.

The present invention also relates to a kit comprising a nucleic acid encoding the hook fusion protein, a vector system, a viral particle system, or a host cell as herein defined.

The present invention also relates to a hook fusion protein, a nucleic acid system, a vector system, a viral particle system, a host cell or a kit, for use as a medicament.

The present invention also relates to the use of a hook fusion protein, a nucleic acid or a system, a vector, a viral particle system, a host cell or a kit for controlling the trafficking of a target fusion protein, wherein said target fusion protein is a membrane protein comprising a hook-binding domain

DETAILED DESCRIPTION

Definitions

Before the present proteins, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

The full name of amino acids is used interchangeably with the standard three letter and one letter abbreviations for each in this disclosure. For the avoidance of doubt, those are: Alanine (Ala, A), Arginine (Arg, R), Asparagine (Asn, N), Aspartic acid (Asp, D), Cysteine (Cys, C), Glutamic Acid (Glu, E), Glutamine (Gln, Q), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), Valine (Val, V).

As used herein, the term "in vitro" refers to events that occur in an artificial environment, e.g., in a test tube or reaction vessel, in cell culture, in a Petri dish, etc., rather than within an organism (e.g., animal, plant, or microbe). The term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The "isolated" products of this invention, including isolated nucleic acids, proteins, polypeptides, and antibodies are not products of nature (i.e., "non-naturally occurring"). Rather, the "isolated" nucleic acids, proteins, polypeptides, and antibodies of this invention are "man-made" products. The "isolated" products of this invention can be "markedly different" or "significantly different" from products of nature. By way of non-limiting example, the isolated nucleic acids may be purified, recombinant, synthetic, labeled, and/or attached to a solid substrate. Such nucleic acids can be markedly different or significantly different than nucleic acids that occur in nature. By way of further non-limiting example, the "isolated" proteins, polypeptides, and antibodies of this invention may be purified, recombinant, synthetic, labeled, and/or attached to a solid substrate. Such proteins, polypeptides, and antibodies can be markedly different or significantly different from proteins, polypeptides, and antibodies that occur in nature.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The protein or polypeptide can be purified. Preferably, the purified protein or polypeptide is more than 50%, 75%, 85%, 90%, 95%, 97%, 98%, or 99% pure. Within the context of this invention, a purified protein that is more than 50% (etc.) pure means a purified protein sample containing less than 50% (etc.) other proteins. For example, a sample of a protein comprising can be 99% pure if it contains less than 1% contaminating host cell proteins.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long, or at least 100 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, "recombinant" may refer to a biomolecule, e.g., a gene or protein, or to a cell or an organism. The term "recombinant" may be used in reference to cloned DNA isolates, chemically synthesized polynucleotides, or polynucleotides that are biologically synthesized by heterologous systems, as well as proteins or polypeptides and/or RNAs encoded by such nucleic acids. A "recombinant" nucleic acid is a nucleic acid linked to a nucleotide or polynucleotide to which it is not linked in nature and/or if it contains any modifications that do not naturally occur to the corresponding nucleic acid in a genome. A "recombinant" protein or polypeptide may be (1) a protein or polypeptide linked to an amino acid or polypeptide to which it is not linked in nature; and/or (2) a protein or polypeptide made by transcription and/or translation of a recombinant nucleic acid. Thus, a protein synthesized by a microorganism is recombinant, for example, if it is synthesized from an mRNA synthesized from a recombinant nucleic acid present in the cell. A "recombinant" cell is a cell comprising a "recombinant" biomolecule. For example, a T cell that comprises a "recombinant" nucleic acid is a "recombinant" cell. A "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments, fragments are at least 10, 15, 20, or 25 nucleotides long, or at least 20, 30, 40, 50, 60, 70, 80, 90, 100, 1 10, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

The nucleic acid can be purified. Preferably, the purified nucleic acid is more than 50%, 75%, 85%, 90%, 95%, 97%, 98%, or 99% pure. Within the context of this invention, a purified nucleic acid that is at least 50% pure means a purified nucleic acid sample containing less than 50% other nucleic acids. For example, a sample of a plasmid can be at least 99% pure if it contains less than 1% contaminating bacterial DNA.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

As used herein a "functional variant" of a given protein includes the wild-type version of said protein, a variant protein belonging to the same family, a homolog protein, or a truncated version, which preserves the functionality of the given protein. Typically the functional variant exhibit at least 70%, 75%, 80%, 85%, 90%, 95%, 97%, 98%, or 99% amino acid identity with the given protein.

As used herein, a "regulatory sequence" also named an "expression control sequence" refers to polynucleotide sequences which affect the expression of coding sequences to which they are operatively linked. Expression control sequences or regulatory sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" (also interchangeably named regulatory sequences) is intended to encompass, at a minimum, any component whose presence is essential for expression, and can also encompass an additional component whose presence is advantageous, for example, leader sequences and fusion partner sequences.

As used herein, "operatively linked" or "operably linked" to a linkage in which the expression control sequence (e.g.: regulatory sequences) is contiguous with the gene of interest to control its expression of the gene of interest. This term also include expression control sequences that act in trans or at a distance to control the expression of the gene of interest.

As used herein, the term "vector", "transfer vector" "recombinant transfer vector", or "gene transfer vector" is intended to mean a nucleic acid molecule capable of transporting a foreign nucleic acid (such as the polynucleotide or the nucleic acid encoding a hook fusion protein or the target fusion protein) to which it is linked.

One type of vector which can be used in the present invention includes, in a non-limiting manner, a linear or circular DNA or RNA molecule consisting of chromosomal, non-chromosomal, synthetic or semi-synthetic nucleic acids, such as in particular a cosmid, artificial chromosomes such as a bacterial artificial chromosome (BAC) or a yeast artificial chromosome (YAC), a viral vector, a plasmid or an RNA vector. One of skill in the art would be well equipped to construct a vector through standard recombinant techniques, which are described in Sambrook et al. (1989) and Ausubel et al. (1994), both incorporated herein by reference.

Numerous vectors into which a nucleic acid molecule can be inserted, in order to introduce it into and maintain it in a eukaryotic host cell including hematopoietic cell, are known per se; the choice of an appropriate vector depends on the use envisioned for this vector (for example, replication of the sequence of interest, expression of this sequence, maintaining of this sequence in extrachromosomal form, or else integration into the chromosomal material of the host), and also on the nature of the host cell.

A "plasmid," generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Naked nucleic acid vectors such as plasmids are usually combined with a substance which allows them to cross the host cell membrane, such as a transporter, for instance a nanotransporter or a preparation of liposomes, or of cationic polymers. Alternatively, a naked nucleic acid may be introduced into said host cell using physical methods such as electroporation or microinjection. In addition, these methods can advantageously be combined, for example using electroporation combined with liposomes.

Another type of vector is a viral vector, wherein additional DNA segments may be ligated into the viral genome. Viral vectors are by nature capable of penetrating into cells and delivering polynucleotide(s) of interest into cells, according to a process named as viral transduction. Therefore, the polynucleotide sequences of interest are introduced into cells by contacting the recombinant viral vector with said cells. Viral vectors include retrovirus, adenovirus, adeno-associated virus (AAV), herpes virus, poxvirus, and other virus vectors. Retrovirus includes in particular type c retrovirus, human T cell leukemia virus (HTLV-1, HTLV-2) and lentivirus. Lentivirus includes in particular human immunodeficiency virus, including HIV type 1 (HIV1) and HIV type 2 (HIV2), feline immunodeficiency virus (FIV), bovine immunodeficiency virus (BIV), equine immunodeficiency virus (FIV), simian immunodeficiency virus (SIV), visna-maedi and caprine arthritis-encephalitis virus (CAEV).

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome.

Moreover, certain vectors are capable of directing the expression of genes or nucleic acid sequences (i.e. encoding the hook fusion protein and/or the target fusion protein) to which they are operatively linked. Such vectors are referred to herein as "recombinant expression vectors" (or simply "expression vectors"). Expression vectors can contain a variety of "control sequences," which refer to nucleic acid sequences necessary for the transcription and possibly translation of an operably linked coding sequence in a particular host organism.

As used herein, the term "mammal" refers to any member of the taxonomic class mammalia, including placental mammals and marsupial mammals. Thus, "mammal" includes humans, primates, livestock, and laboratory mammals. Exemplary mammals include a rodent, a mouse, a rat, a rabbit, a dog, a cat, a sheep, a horse, a goat, a llama, cattle, a primate, a pig, and any other mammal. In some embodiments, the mammal is at least one of a transgenic mammal, a genetically-engineered mammal, and a cloned mammal.

As used herein, "a hook protein" is usable in a system referred to as RUSH (retention using selective hooks) (see Boncompain et al., Nat. Methods 9:493-498, 2012, as well as WO2010142785 and WO201612623, which also describe the RUSH system). Typically the hook protein is a fusion protein, which allows retaining a target protein containing a corresponding hook-binding domain in a donor compartment (i.e. the compartment from which the target protein originates) by a specific interaction with said target protein. When released from the interaction with the hook protein, the target protein is free to traffic toward its target compartment (i.e. the compartment to which the target protein is targeted). To control these two states, the specific interaction between the target protein and the hook is mediated by a reversible interaction between two interaction domains. In one embodiment, the interaction only occurs in the presence of a given ligand ("molecule-dependent" set-up, "MD"). In another embodiment, the interaction occurs by default and can be disrupted by a given ligand ("interaction-by-default" setup, "ID"). The removal or addition of the ligand acts like a switch to allow the synchronous release of the target protein from the donor compartment. When referring to a hook protein and a target fusion protein in a nucleic acid system, a vector system, an isolated cell, a kit or in a method or use of the invention, it is intended that the target fusion protein comprises a hook-binding domain which corresponds to the hook domain of said hook fusion protein. Suitable hook domain/hook-binding domain couples are described below.

Hook Fusion Protein:

The present invention provides a new hook protein, which is a fusion protein comprising:
  a hook domain
  at least one cytoplasmic carboxy terminal endoplasmic reticulum (ER) retention signal and/or at least one cytoplasmic amino terminal endoplasmic reticulum (ER) retention signal;
wherein the hook fusion protein of the invention is a soluble protein that localizes in the cytoplasm.

By soluble protein it is intended herein that the hook protein does not comprise a transmembrane domain Said protein is further a cytoplasmic protein.

This soluble hook protein allows controlling the localization of a given target membrane protein comprising a hook-binding domain, according to the presence or absence of a specific ligand. The previously described hooks were stably anchored by default in the donor compartment (typically the ER or the Golgi apparatus). To the contrary, the new hook of the invention remains soluble in the cytosol in the absence of binding to the target protein containing the hook-binding domain. It can therefore retrieve any target membrane protein that leaked out from the ER to the cytosol. When bound to the target protein, the hook protein retains the target protein in the endoplasmic reticulum (ER) (i.e. the ER lumen or the ER membrane). Upon addition or removal of the ligand, the target protein is released. The release of said target protein is fast and synchronous for all the molecules of the target protein.

In one embodiment, the interaction between the hook protein and the target protein occurs in a molecule-dependent way in the presence of a specific ligand ("molecule-dependent" or "MD" setup), and can be reversed by wash-out of the ligand. According to this embodiment, the interaction between the hook domain of the hook protein and the hook-binding domain of the target protein occurs only in the presence of a given ligand. This embodiment is called the "MD" mode. Regulation of the interaction, which results in the release of the target protein from the hook fusion protein, can be carried out by wash-out of the specific ligand with or without competition by a competitor, which competes with the specific ligand for binding to either the hook domain of the hook protein or the hook-binding domain of the target protein.

In this embodiment, the MD interaction couple (hook domain/hook binding domain or hook-binding domain/hook domain) can be the FKBP-FK506 binding domain 12/FKBP-rapamycin associated protein (FKBP 12/FRAP). FKBP12 (also known as FKBP1A) is a FK506 and rapamycin-binding protein of 12 kD (Standaert et al, 1990; Maki et al, 1990). FRAP is a 245 kD which binds to the FKBP12-rapamycin associated protein (Brown et al., 1994). In a preferred embodiment of the RUSH system, only the rapamycin-binding domains are used. In this embodiment, the interaction occurs only in the presence of rapamycin or analogues thereof as a specific ligand L. Such ligand can be any ligand able to mediate the interaction between FKBP 12 and FRAP and can be, in particular, selected from the group consisting of FK1 012, FK-CsA and rapamycin. Analogs of Rapamycin (Rapalog) may also be used in conjunction with mutants of FKBP 12 and FRAP domains (like AP21967, ARIAD Pharmaceutical Inc.) These ligands have been extensively used in systems for controlling gene expression at the transcriptional level (see Clackson 1997 for review). Rapamycin (commercially available from Sigma-Aldrich for example) can be used at concentrations ranging from 1.5 nM to 200 nM, preferably from 1.52 nM to 12.2 nM, even more preferably at about 3.1 nM. FK506 can be used as a competitor and can therefore be added when rapamycin is removed, in order to disrupt the interaction between FKPB 12 and FRAP. FK506 (commercially available from Cayman for example) can be used at concentrations ranging from 390 µM to 1.25 µM, preferably at about 3.3 µM. Other competitors can be used, such as Ascomycin (Sigma-Aldrich) at concentrations ranging from 12.5 µM to 1.6 µM, preferably at about 3.3 µM or SLF (Cayman) at concentrations ranging from 28.6 µM to 3.6 µM and preferably at about 5 µM.

Alternatively, the MD interaction couple (hook domain/hook binding domain or hook-binding domain/hook domain) can be FKBP-rapamycin binding domain 12/a protein that binds to FKBP12 in a rapamycin-dependent manner. In this embodiment, the interaction occurs only in the presence of rapamycin or analogues thereof as a ligand L. Document U.S. Pat. No. 6,492,106 discloses methods for identifying such proteins that bind to FKBP 12 in a rapamycin-dependent manner In a preferred embodiment, the interaction between the hook protein and the target protein occurs by default in the absence of a specific ligand ("interaction by default" or "ID" set-up) and is inhibited in the presence of such specific ligand. In this embodiment, the interaction between the hook domain of the hook protein and the hook-binding domain of the target protein occurs by default, in the absence of any ligand. The interaction is disrupted by the presence of a specific ligand.

Suitable ID interaction domain couples (hook domain/hook binding domain or hook-binding domain/hook domain) can be selected for example from the group consisting of Streptavidin/SBP tag, Ftsz/ZipA, HPV E1/E2, recombinant antibody/epitope, recombinant epitope/hapten, proteinA/IgG domain, Fos/Jun. Interaction domain couples for which a specific ligand inhibiting the interaction is already known are preferred.

In one embodiment, the ID interaction domain couple (hook domain/hook binding domain or hook-binding domain/hook domain) is FtsZ/ZipA. FtsZ and ZipA are bacterial proteins which form part of the septal ring which forms during the replication of certain Gram-negative bacteria. Their interaction can be disrupted by addition of a small molecule named "compound 1" as a ligand L (see Wells et al. 2007 for review.). Compound 1 (Wyeth Research (NY, USA)) can be used at concentrations ranging between 10 and 100 µM.

In the preferred embodiment according to the invention, the ID interaction domain couple (hook domain/hook binding domain or hook-binding domain/hook domain) is streptavidin/streptavidin binding peptides (SBPs) and free biotin can be used as a ligand. Streptavidin is a bacterial protein that binds with very high affinity to vitamin D-biotin. In vitro selection approaches have led to the discovery of synthetic peptides (SBPs) that bind to Streptavidin and that can be competed out by biotin or biotin mimetic molecules from the ALiS (Artificial ligands of streptavidin) series (these compound are described in Terai T, Kohno M, Boncompain G, Sugiyama S, Saito N, Fujikake R, Ueno T, Komatsu T, Hanaoka K, Okabe T, Urano Y, Perez F, Nagano T. "Artificial Ligands of Streptavidin (ALiS): Discovery, Characterization, and Application for Reversible Control of Intracellular Protein Transport". J Am Chem Soc. 2015 Aug. 26; 137(33):10464-7 and in Tachibana R, Terai T, Boncompain G, Sugiyama S, Saito N, Perez F, Urano Y. "Improving the Solubility of Artificial Ligands of Streptavidin to Enable More Practical Reversible Switching of Protein Localization in Cells". Chembiochem: a European journal of chemical biology. 2017 Feb. 16; 18(4):358-62).

Accordingly, a hook protein of the invention preferably comprises as a hook domain a streptavidin protein sequence. Such a hook protein according to the invention is able to control the trafficking of any membrane protein comprising a streptavidin-binding domain (such as SBP).

Preferably, the hook comprises a streptavidin protein sequence, most preferably core streptavidin, such as described in U.S. Pat. No. 5,672,691, which is hereby incorporated by reference.

Streptavidin protein sequences suitable to the present invention typically encompass the Streptavidin protein sequences as described below:

(SEQ ID NO: 1)
MDPSKDSKAQVSAAEAGITGTWYNQLGSTFIVTAGADGALTGTYESAVG

NAESRYVLTGRYDSAPATDGSGTALGWTVAWKNNYRNAHSATTWSGQYV

GGAEARINTQWLLTSGTTEAN AWKSTLVG H DTFTKVKPSAAS I

DAAKKAGVN NG N PLDAVQQ, wt streptavidin sequence)

Suitable hook domains can also be selected from low affinity streptavidin mutant sequences. Such streptavidin mutant sequences can bind reversibly to biotin while keeping a high affinity for the streptavidin-binding protein (SBP). Accordingly, streptavidin protein sequences suitable for use in the present invention also encompass streptavidin sequences as described in Wu et al., PLoS ONE 8(7): e69530 (2013) and WO2013/038272 U.S. Pat. No. 9,353,161B2, which are hereby incorporated by reference. In particular, streptavidin sequences wherein the glycine at aa 49 (including the first methionine amino acid, or amino acid 48 if excluding said first methionine) of SEQ ID NO:1 or SEQ ID NO: 2 is replaced with a bulkier residue (e.g., threonine) to reduce the biotin binding affinity without affecting the SBP binding affinity are encompassed. Another mutation can also be introduced to further favor SBP binding over biotin (mutation S27A).

In particular, the skilled person in the art can create a single mutant containing a single mutation of serine to alanine substitution at residue 27, and a double mutant containing this change as well as a glycine to threonine substitution at residue 48 corresponding to full-length wild-type streptavidin (SEQ ID NO: 1). Although threonine is exemplified as a replacement residue for glycine 48, other residues with bulky side chains and high propensity for turns (Pt>0.83) are contemplated (e.g., Asp, Glu, Asn, Gln).

A monomeric core Streptavidin has also been constructed by Wu and Wong (2005) (see U.S. Pat. No. 7,265,205 B2 and SEQ ID NO: 2 below).

(SEQ ID NO: 2)
MDPSKDSKAQVSAAEAGITGTWYNQLGSTFIVTAGADGALTGTYESAVG

NAESRYTLTGRYDSAPATDGSGTALGWRVAWKNNYRNAHSATTWSGQYV

GGAEARINTQWTLTSGTTEANAWKSTLRGHDTFTKVKPSAASIDAAKKA

GVNN GNPLDAVQQ.

As used herein, "Streptavidin" can refer to all forms of streptavidin (tetramer, core or monomer). In a preferred embodiment, a streptavidin sequence comprises the amino acid sequence as set forth in SEQ ID NO: 1 or 2 as well as the low affinity variants as described above, or a variant thereof having at least 80% identity with SEQ ID NO: 1 or SEQ ID NO: 2, preferably 85%, 90, 95, 96, 97, 98, 99, 99.5% identity with such sequences. "Streptavidin" can also encompass Streptavidin homologs from other species, such as avidin or rhizavidin. Mutant of these natural biotin-binding proteins may also be used.

The endoplasmic reticulum (ER) retention domain according to the invention can be any protein or protein domain which is a resident of the ER. The term "resident", when used herein applied to a given protein or domain and to a given compartment, is intended to mean that said protein or domain is in majority located in a given compartment. Typically, at least 70%, preferably at least 75%, 80%, 85%, 90%, 95%, 96%, 97%, 98%, 99% of said protein or domain is located in said compartment at steady-state in a host cell.

Suitable carboxy-terminal endoplasmic reticulum (ER) retention sequence are typically C-terminal dilysine-based motifs, such as the KXKXX sequence (SEQ ID NO: 3) and the KKXX sequence (SEQ ID NO: 4), with X being any amino acid.

Suitable amino-terminal endoplasmic reticulum (ER) retention sequences can be selected from fragments comprising the localization domains of an isoform of the invariant chain which resides in the ER (Ii, a type II protein), of Ribophorin I or II (Strubin et al., 1986; Strubin et al., 1984; Schutze et al., 1994; Fu et al. 2000), of SEC61, or of cytochrome b5 (Bulbarelli et al., 2002). Preferred amino-terminal endoplasmic reticulum (ER) retention sequences are fragments comprising the localization domains of an isoform of the invariant chain which resides in the ER (Ii). Typically a suitable fragments comprising the localization domains of an isoform of the invariant chain which resides in the ER (Ii) comprises, or consists in, the first 46 amino acids starting from the N-terminal portion of the Ii protein. Said fragment is represented by the amino acid of SEQ ID NO: 5:

MHRRRARACREDQKPV<u>T</u>DDQRDLISNNEQLPMLGRRPGAPESKCSR.

In one alternative sequence the "T" amino acid in position 17 (from the left of the sequence SEQ ID NO: 5) might be replaced by an "I" (SEQ ID NO: 14).

Preferably, the hook protein according to the present invention further comprises an endocytosis signal. Such a hook protein is highly advantageous as it allows retrieving target proteins from the plasma membrane. Such hook allows a fully reversible control of the subcellular localization of the target protein. Indeed, the target protein may be retained in the ER compartment, let free to resume its journey to the plasma membrane or retrieved from the plasma membrane.

Typically the endocytosis signal (also named internalization signal) allows clathrin-dependent endocytosis of the target membrane protein. Suitable internalization signals include endocytotic signals as described in Traub L M, Bonifacino J S. "Cargo recognition in clathrin-mediated endocytosis". Cold Spring Harb Perspect Biol. 2013 Nov. 1; 5(11):a016790. Typically, linear motifs consisting of short arrays of invariant and variant amino acids, including "tyrosine-based" YXXØ (SEQ ID NO: 15) and [FY]XNPX[YF] (SEQ ID NO: 16) motifs, and "dileucine-based" [DE]XXXL[LI] (SEQ ID NO: 17) motifs, acidic clusters and [YF]XNPX[YF] (SEQ ID NO: 18) motifs are well-suited to the present invention. Typically the signal is a C terminal endocytosis signal. Suitable endocytosis signals according to the invention include fragments of the LAMP1 protein sequence containing the endocytosis signal, or comprises the [DE]XXXLL (SEQ ID NO: 29) consensus sequence. In this notation, amino acids are represented in single-letter code, X indicates any amino acid, Ø indicates an amino acid with a bulky hydrophobic side chain, and the brackets mean that either amino acid is allowed at that position. The endocytosis signal of the invention may be selected from the group consisting of SEQ ID NO: 15 to 18. Preferably the endocytosis signal is YXXI (SEQ ID NO: 28) (X being any amino acid).

The hook protein typically comprises at least one ER retention signal and at least one retention signal. In one embodiment the hook protein comprises at least a cytoplasmic carboxy terminal ER retention signal and/or a cytoplasmic amino terminal ER retention signal and an endoplasmic retention signal. The hook protein can comprise both a cytoplasmic carboxy terminal ER retention signal and a cytoplasmic amino terminal ER retention signal in addition to the endocytosis signal.

Nucleic Acids and Vectors of the Invention

The present invention also encompasses a nucleic acid system comprising one or more nucleic acids and comprising (a) at least one nucleic acid sequence encoding a hook fusion protein as previously, defined and wherein the hook fusion protein localizes in the ER when bound to a target fusion membrane protein.

The nucleic acid can be single-stranded or double-stranded. The nucleic acid can be an RNA or DNA molecule. Preferred nucleic acids encode an amino acid sequence of at least one of the SEQ ID NOs detailed herein.

As a matter of example, the nucleic acid comprises one or more of the following nucleic acid sequences encoding a hook fusion protein as previously described:

Soluble cytoplasmic hook proteins having N terminal ER retention signal (SEQ ID NO: 6)
ATGCACAGGAGGAGAGCCAGGGCCTGTCGGGAAGATCAAAAGCCAGTCA CtGATGATCAGCGCGACCTTATCTCCAACAATGAGCAACTGCCCATGCT

GGGCCGGCGGCCTGGGGCCCCGGAGAGCAAGTGCAGCCGCGCTAGCGAC

CCTAGCAAAGACTCAAAAGCTCAGGTGTCCGCTGCCGAGGCTGGCATTA

CTGGAACATGGTACAATCAGCTCGGGAGCACCTTTATTGTGACTGCTGG

AGCCGATGGAGCCCTCACCGGAACATACGAATCTGCTGTGGGAAACGCC

GAATCACGGTACGTCCTCACTGGCCGATACGATAGTGCCCCTGCCACCG

ACGGATCTGGGACTGCCCTGGGATGGACTGTCGCTTGGAAAAACAACTA

CCGGAATGCTCATTCTGCCACAACATGGAGTGGACAGTACGTGGGAGGC

GCTGAGGCTAGAATCAATACACAGTGGCTGCTCACATCTGGCACAACCG

AGGCAAATGCTTGGAAATCCACCCTGGTGGGACATGACACATTCACCAA

AGTGAAACCCTCCGCCGCTTCAATTGATGCCGCCAAAAAAGCCGGAGTC

AACAACGGCAATCCTCTGGATGCCGTCCAGCAGTACCCCTACGACGTGC

CCGACTACGCCGCCGGCTACCAGACCATC.

The sequence SEQ ID NO: 6 having the following features:
HA-tag: nucleotides [622-648]
LAMP1: nucleotides [649-666]
Streptavidin: nucleotides [146-621]
mini-Ii-46aa: nucleotides [1: 138]
Or (SEQ ID NO: 7)
ATGCACAGGAGGAGAGCCAGGGCCTGTCGGGAAGATCAAAAGCCAGTCA

TCGATGATCAGCGCGACCTTATCTCCAACAATGAGCAACTGCCCATGCT

GGGCCGGCGCCCTGGGGCCCCGGAGAGCAAGTGCAGCCGCCTCGAGGAC

CCTAGCAAAGACTCAAAAGCTCAGGTGTCCGCTGCCGAGGCTGGCATTA

CTGGAACATGGTACAATCAGCTCGGGAGCACCTTTATTGTGACTGCTGG

AGCCGATGGAGCCCTCACCGGAACATACGAATCTGCTGTGGGAAACGCC

GAATCACGGTACGTCCTCACTGGCCGATACGATAGTGCCCCTGCCACCG

ACGGATCTGGGACTGCCCTGGGATGGACTGTCGCTTGGAAAAACAACTA

CCGGAATGCTCATTCTGCCACAACATGGAGTGGACAGTACGTGGGAGGC

GCTGAGGCTAGAATCAATACACAGTGGCTGCTCACATCTGGCACAACCG

AGGCAAATGCTTGGAAATCCACCCTGGTGGGACATGACACATTCACCAA

AGTGAAACCCTCCGCCGCTTCAATCGATGCCGCCAAAAAAGCCGGAGTC

AACAACGGCAATCCTCTGGATGCCGTCCAGCAG.

The sequence SEQ ID NO: 7 having the following features:
Core Streptavidin: nucleotides [145-621]
mini Ii: nucleotides [1-138]

Soluble Cytoplasmic Hook Proteins Having C Terminal ER Retention Signal (SEQ ID NO: 8)
ATGGACCCCAGCAAGGACAGCAAGGCCCAGGTGAGCGCCGCCGAGGCCG

GCATCACCGGCACCTGGTACAACCAGCTGGGCAGCACCTTCATCGTGAC

CGCCGGCGCCGACGGCGCCCTGACCGGCACCTACGAGAGCGCCGTGGGC

AACGCCGAGAGCAGATACGTGCTGACCGGCAGATACGACAGCGCCCCCG

CCACCGACGGCAGCGGCACCGCCCTGGGCTGGACCGTGGCCTGGAAGAA

CAACTACAGAAACGCCCACAGCGCCACCACCTGGAGCGGCCAGTACGTG

GGCGGCGCCGAGGCCAGAATCAACACCCAGTGGCTGCTGACCAGCGGCA

CCACCGAGGCCAACGCCTGGAAGAGCACCCTGGTGGGCCACGACACCTT

CACCAAGGTGAAGCCCAGCGCCGCCAGCATCGACGCCGCCAAGAAGGCC

GGCGTGAACAACGGCAACCCCCTGGACGCCGTGCAGCAGGGCGGatcCT

ACCCCTACGACGTGCCCGACTACGCCGCCGGCTACCAGACCATCAAGAA

GACCAAC

The sequence SEQ ID NO: 8 having the following features:
Streptavidin: [1: 480]
(GGS)-HA: [481: 516]
LAMP1 tail: [517: 534]
ER Retention: [535: 546]
HA tag: [490: 516]

In a preferred embodiment the nucleic acid system further comprises (b) at least one nucleic acid sequence encoding a target fusion membrane protein comprising a hook-binding domain.

Said at least one nucleic acid sequences (a) and (b) can be located on the same or different nucleic acids.

Preferably, the hook fusion protein comprises a streptavidin domain and the target fusion protein comprises a streptavidin-binding domain. In a preferred embodiment, the present invention relates to a nucleic acid encoding at least one hook fusion protein as previously described and a nucleic acid sequence encoding a target fusion membrane protein comprising a hook-binding domain.

Target fusion membrane proteins, which are well suited to the present invention, are described in the following sections. Thus the present invention also encompasses nucleic acids encoding such target proteins.

A hook-binding domain is a domain that reversibly binds directly or indirectly to a hook domain (as previously defined) of a hook fusion protein inside a cell and which binding leads to the retention of the target protein in the ER under appropriate conditions. Suitable hook domains and corresponding hook-binding domain have been described in the previous section (see hook fusion protein). Therefore, an appropriate hook domain can be selected from the above mentioned example depending on the selected hook domain of the hook protein.

In a preferred embodiment, the hook domain of the hook protein comprises a streptavidin sequence a previously mentioned. Accordingly, the hook-binding domain comprises or consists in a streptavidin binding peptide (SBP). Preferably, the hook-binding domain comprises the following SBP amino acid sequence:

(SEQ ID NO: 9)
MDEKTTGWRGGHVVEGLAGELEQLRARLEHHPQGQREP, or is encoded by the nucleic acid sequence:

(SEQ ID NO: 10)
ATGGACGAGAAAACCACCGGCTGGCGGGGAGGCCACGTGGTGGAAGGAC
TGGCCGGCGAGCTGGAACAGCTGCGGGCCAGACTGGAACACCACCCCCA
GGGCCAGAGAGAGCCC.

Shorter SBP fragments, deleted at their N-terminus and C-terminus may be used with identical efficacy. See Barrette-Ng, I. H., S. C. Wu, W. M. Tjia, S. L. Wong, and K. K. Ng. 2013, The structure of the SBP-Tag-streptavidin complex reveals a novel helical scaffold bridging binding pockets on separate subunits, Acta crystallographies. Section D, Biological crystallography 69:879-887.

Well-suited short SBP (sSBP) versions can have the following sequences:

(SEQ ID NO: 11)
GHVVEGLAGELEQLRARLEHHPQGQREP,
or (SEQ ID NO: 12)
GGHVVEGLAGELEQLRARLEHHPQGQREP

The target protein according to the invention can be any protein for which is desirable to control the intracellular trafficking from a given donor compartment to a final target compartment, in particular for which it is desirable to reversibly control cell membrane expression.

Examples of target proteins can be, but are not limited to: plasma membrane markers and Major Histocompatibility (MHC) molecules such as CD4, CD8; viral glycoproteins such as VSVG and HA; signal transduction proteins; Transporter proteins like the multidrug resistance protein ABCB 1. Typically, the target protein can be any molecule of therapeutic interest, for which it is desirable to tightly regulate the intracellular trafficking in order to obtain a therapeutic effect. Conversely, the target protein can be a pathological molecule, whose pathological effect is linked to cell membrane expression. In a preferred embodiment, the target protein is a chimeric antigen receptor (CAR).

In one embodiment, the invention encompasses a chimeric antigen receptor (CAR) comprising an extracellular antigen-binding domain (binding domain), a hinge and transmembrane domain (transmembrane domain); a hook-binding domain as above defined; and an intracellular signaling domain (activation domain) The CAR can contain one, two, three, or more of each of these domains. The invention encompasses individually all possible combinations of the specific polypeptides and fragments thereof recited herein.

Typically, the binding domain of a CAR according to the invention comprises an antibody that binds specifically to a human polypeptide. The term "antibody" is meant to include polyclonal antibodies, monoclonal antibodies, fragments thereof, such as F(ab')2 and Fab fragments, single-chain variable fragments (scFvs), single-domain antibody fragments (VHHs or Nanobodies, preferably camelid), and bivalent and trivalent antibody fragments (diabodies and triabodies).

Preferably, the antibody is a single-chain Fv antibody or a nanobody. In one embodiment, the antibody is monospecific. In one embodiment, the antibody is multispecific for 2, 3, or 4 polypeptides, for example bispecific.

Antibodies can be synthetic, monoclonal, or polyclonal and can be made by techniques well known in the art. Such antibodies specifically bind to human proteins via the antigen-binding sites of the antibody (as opposed to non-specific binding). Human proteins, polypeptide fragments, and peptides can be employed as immunogens in producing antibodies immunoreactive therewith. The human proteins, polypeptides, and peptides contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrance, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art.

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14: 139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240: 1041 1043, 1988; Liu et al., PNAS 84:3439 3443, 1987; Liu et al., J. Immunol. 139:3521 3526, 1987; Sun et al. PNAS 84:214 218, 1987; Nishimura et al., Cane. Res. 47:999 1005, 1987; Wood et al., Nature 314:446 449, 1985; and Shaw et al., J. Natl. Cancer Inst. 80: 1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239: 1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

The activation domain of a CAR according to the invention typically comprises CD3-ζ or Fc receptor γ amino acid sequences (see notably Sadelain et al., Cancer Discov. 2013 April; 3(4): 388-398, which is hereby incorporated by reference) or a CD3-ζ chain and at least one cytoplasmic domain of a costimulatory receptor. For example, costimulatory receptors include CD28, 4-1 BB (CD137), DAP10, DAP12, OX40 (CD134), ICOS, CD27, and CD40L.

Preferably, the CAR comprises a fragment of at least 50, 60, 70, 80, 90, 100, 1 10, 120, 150, or 200 amino acids of at least one of the following proteins having T-cell activating activity: CD3-ζ chain and the costimulatory receptors CD28, 4-1 BB (CD137), DAP10, DAP12, OX40 (CD134), ICOS, CD27, and CD40L.

In various embodiments, the CAR comprises a fragment of at least 20, 30, 40, 50, 60, 70, 80, 90, 100, 110, 120, 150, or 200 amino acids that shares at least than 90%, preferably more than 95%, more preferably more than 99% identity with the following proteins having T-cell activating activity: CD3-ζ chain and the costimulatory receptors CD28, 4-1 BB (CD137), DAP10, DAP12, OX40 (CD134), ICOS, CD27, and CD40L.

In various embodiments, the activation domain of the CAR comprises one, two, three, or more fragments of at least 20, 30, 40, 50, 60, 70, 80, 90, 100, 110, 120, 150, or 200 amino acids that share at least than 90%, preferably more than 95%, more preferably more than 99% identity with the following proteins having T-cell activating activity: CD3-ζ chain and the costimulatory receptors CD28, 4-1 BB (CD137), DAP 10, DAP12, OX40 (CD134), ICOS, CD27, and CD40L.

The invention encompasses a CAR comprising a transmembrane (TM) domain, preferably a fragment of at least 20, 30, 40, 50, 60, 70, 80, 90, 100, 1 10, 120, 150, or 200 amino acids, most preferably of at least one of CD28, CD3z, CD8, CD4, FcRy, DAP10 and DAP12 transmembrane region.

Preferred CARs according to the above-mentioned description and nucleic acids encoding such CARs are described in WO201612623. In one embodiment, the nucleic acid encoding the hook fusion protein as previously described further comprises a nucleic acid sequence encoding a CAR as described in WO201612623.

In a distinct embodiment of the present invention, the target fusion protein is an "NKG2D-based CAR" comprising: the full NKG2D or a functional variant thereof, at least an activation domain, and a hook-binding domain. The intracellular domain (i.e. the cytoplasmic region) of the full NKG2D protein or functional variant thereof can be fused to the activation domain or to the hook-binding domain. Preferably, the intracellular domain (i e the cytoplasmic region) of the full NKG2D protein or functional variant thereof is fused to the hook-binding domain.

Natural killer (NK) cells attack tumor and virally infected cells in the absence of major histocompatibility complex (MHC) restriction, using a combination of signals from activating and inhibitory receptors. One of these activating receptors is NKG2D, which is expressed on all NK cells, NKT cells, γδ T cells, and some CD8+ αβ T cells. Ligands for human NKG2D include MHC class I chain-related A (MICA), MICB, and several UL-16-binding proteins (ULBPs). It has been found that NKG2D ligands are primarily expressed on tumor cells but not on most normal tissues. Thus, the NKG2D receptor-NKG2D ligand system provides a relatively specific system for immune cells to recognize tumor cells.

NKG2D according to the invention is preferably the human NKG2D (UNIPROT ref P26718) encoded by the KLRK1 gene (killer cell lectin like receptor K1) (Gene ID: 22914).

Suitable activation domains and hook-binding domains have been described previously. Preferably the activation domain comprises a CD3-ζ chain and/or at least one cytoplasmic domain of a costimulatory receptor as defined above. For example, costimulatory receptors include CD28, 4-1 BB (CD137), DAP10, DAP12, OX40 (CD134), ICOS, CD27, and CD40L, as also defined above. Preferably also, the hook-binding domain is a streptavidin binding sequence as previously defined.

As a matter of example, a nucleic acid of the invention encoding a hook fusion protein as previously described can further encompasses a nucleic acid sequence encoding an NKG2D-based CAR comprising the following construct: CD3z-SBP-NKG2D.

A nucleic acid sequence encoding a well-suited CD3z-SBP-NKG2D construct is the following:

(SEQ ID NO: 13)
ATGAGAGTGAAGTTCAGCAGGAGCGCAGACGCCCCCGCGTACCAGCAGG

GCCAGAACCAGCTCTATAACGAGCTCAATCTAGGACGAAGAGGAGTA

-continued
```
CGATGTTTTGGACAAGAGACGTGGCCGGGACCCTGAGATGGGGGAAAG

CCGCAGAGAAGGAAGAACCCTCAGGAAGGCCTGTACAATGAACTGCAGA

AAGATAAGATGGCGGAGGCCTACAGTGAGATTGGGATGAAAGGCGAGCG

CCGGAGGGGCAAGGGGCACGATGGCCTTTACCAGGGTCTCAGTACAGCC

ACCAAGGACACCTACGACGCCCTTCACATGCAGGCCCTGCCCCCTCGCG

AATTCCCTGCAGGAGGCCGGCCAGACGAGAAGACCACCGGCTGGAGAGG

CGGCCACGTGGTGGAGGGCCTGGCCGGCGAGCTGGAGCAGCTGAGAGCC

AGACTGGAGCACCACCCCCAGGGCCAGAGAGAGCCCAGCGATCGCGGGT

GGATTCGTGGTCGGAGGTCTCGACACAGCTGGGAGATGAGTGAATTTCA

TAATTATAACTTGGATCTGAAGAAGAGTGATTTTTCAACACGATGGCAA

AAGCAAAGATGTCCAGTAGTCAAAAGCAAATGTAGAGAAAATGCATCTC

CATTTTTTTCTGCTGCTTCATCGCTGTAGCCATGGGAATCCGTTTCAT

TATTATGGTAGCAATATGGAGTGCTGTATTCCTAAACTCATTATTCAAC

CAAGAAGTTCAAATTCCCTTGACCGAAAGTTACTGTGGCCCATGTCCTA

AAAACTGGATATGTTACAAAAATAACTGCTACCAATTTTTTGATGAGAG

TAAAAACTGGTATGAGAGCCAGGCTTCTTGTATGTCTCAAAATGCCAGC

CTTCTGAAAGTATACAGCAAAGAGGACCAGGATTTACTTAAACTGGTGA

AGTCATATCATTGGATGGGACTAGTACACATTCCAACAAATGGATCTTG

GCAGTGGGAAGATGGCTCCATTCTCTCACCCAACCTACTAACAATAATT

GAAATGCAGAAGGGAGACTGTGCACTCTATGCATCGAGCTTTAAAGGCT

ATATAGAAAACTGTTCAACTCCAAATACATACATCTGCATGCAAAGGAC

TGTGTAATTA.
```

The present invention further encompasses a nucleic acid system for the targeting control of a target protein comprising: (a) a nucleic acid sequence encoding a hook fusion protein as previously defined, and (b) a nucleic acid sequence encoding a target fusion protein fused to a hook-binding domain as previously defined. Typically as previously indicated the target fusion protein in a membrane protein and the hook fusion protein localizes in the ER when bound to the target fusion protein. Said nucleic acid sequence (a) and (b) can be included in the same nucleic acid or in separate nucleic acids. Preferably, the hook fusion protein comprises a streptavidin domain and the target fusion protein comprises a streptavidin binding domain. Preferably, also, the target fusion protein is a CAR fusion protein as previously described.

The present invention also encompasses an isolated nucleic acid or nucleic acid system as described above inserted in one or more vector(s).

Vectors of the Invention

The present invention encompasses a vector system comprising one or more vectors comprising
(a) the nucleic acid sequence a hook fusion protein as previously defined, and optionally
(b) a nucleic acid encoding a target fusion protein comprising a hook-binding domain;
wherein the nucleic acids (a) and (b) are located on the same or on separate vectors;

Preferably, as previously mentioned, the hook fusion protein comprises a streptavidin sequence and the target fusion protein comprises a streptavidin-binding domain.

A vector according to the present invention can be a plasmid.

A vector according to the invention is preferably a vector suitable for stable gene transfer and long-term gene expression into mammalian cells, such as by replication of the sequence of interest, expression of this sequence, maintaining of this sequence in extrachromosomal form, or else integration into the chromosomal material of the host. The recombinant vectors are constructed using standard recombinant DNA technology techniques and produced using conventional methods that are known in the art.

In some embodiments, a vector of the invention is an integrating vector, such as an integrating viral vector, such as in particular a retrovirus or AAV vector. Preferably, the viral vector is a lentiviral vector.

Within the context of this invention, a "lentiviral vector" means a non-replicating non-pathogenic virus engineered for the delivery of genetical material into cells, and requiring lentiviral proteins (e.g., Gag, Pol, and/or Env) that are provided in trans. Indeed, the lentiviral vector lacks expression of functional Gag, Pol, and Env proteins. The lentivirus vector is advantageously a self-inactivating vector (SIN vector). The lentiviral vector comprises advantageously a central polypurine tract/DNA FLAP sequence (cPPT-FLAP), and/or insulator sequence (s) such as chicken beta-globin insulator sequence(s) to improve expression of the gene(s) of interest. The lentiviral vector is advantageously pseudotyped with another envelope protein, preferably another viral envelope protein, preferably the vesicular stomatis virus (VSV) glycoprotein. In some preferred embodiments, said lentiviral vector is a human immunodeficiency virus (HIV) vector.

The lentiviral vector may be present in the form of an RNA or DNA molecule, depending on the stage of production or development of said retroviral vectors. The lentiviral vector can be in the form of a recombinant DNA molecule, such as a plasmid, or in the form of a lentiviral vector particle (interchangeably named lentiviral particle in the context of the present invention), such as an RNA molecule(s) within a complex of lentiviral and other proteins.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and Trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two c/s-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells. In one embodiment, the invention encompasses a lentiviral vector comprising a central polypurine tract and central termination sequence referred to as cPPT/

CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (AU3) (Miyoshi H et al, 1998, J Virol. 72(10):8150-7; Zufferey et al., 1998, J V/ro/72(12):9873-80).

Preferably, the vector does not contain an enhancer. In one embodiment, the invention encompasses a lentiviral vector comprising LTR sequences, preferably with a mutated U3 region (AU3) removing promoter and enhancer sequences in the 3' LTR.

The packaging sequence Ψ (psi) can also be incorporated to help the encapsidation of the polynucleotide sequence into the vector particles (Kessler et al., 2007, Leukemia, 21 (9): 1859-74; Paschen et al., 2004, Cancer Immunol Immunother 12(6): 196-203). In one embodiment, the invention encompasses a lentiviral vector comprising a lentiviral packaging sequence Ψ (psi).

Further additional functional sequences, such as a transport RNA-binding site or primer binding site (PBS) or a Woodchuck PostTranscriptional Regulatory Element (WPRE), can also be advantageously included in the lentiviral vector polynucleotide sequence of the present invention, to obtain a more stable expression of the transgene in vivo. In one embodiment, the invention encompasses a lentiviral vector comprising a PBS. In one embodiment, the invention encompasses a lentiviral vector comprising a WPRE and/or an IRES Typically, lentiviral particles refer to the extracellular infectious form of a virus composed of genetic material made from either DNA or RNA (most preferably single stranded RNA) surrounded by a protein coat, called the capsid, and in some cases an envelope of lipids that surrounds the capsid. Thus a lentiviral vector particle (or a lentiviral particle) comprises a lentiviral vector as previously defined in association with viral proteins. The vector is preferably an integrating vector.

The RNA sequences of the lentiviral particle can be obtained by transcription from a double-stranded DNA sequence inserted into a host cell genome (proviral vector DNA) or can be obtained from the transient expression of plasmid DNA (plasmid vector DNA) in a transformed host cell. Appropriate methods for designing and preparing lentiviral particles in particular for therapeutic application are well-known in the art and are for example described in Merten O W, Hebben M, Bovolenta C. Production of lentiviral vectors. Mol Ther Methods Clin Dev. 2016 Apr. 13; 3:16017.

Preferably the lentiviral particles have the capacity for integration. As such, they contain a functional integrase protein. Non-integrating vector particles have one or more mutations that eliminate most or all of the integrating capacity of the lentiviral vector particles. For, example, a non-integrating vector particle can contain mutation(s) in the integrase encoded by the lentiviral pol gene that cause a reduction in integrating capacity. In contrast, an integrating vector particle comprises a functional integrase protein that does not contain any mutations that eliminate most or all of the integrating capacity of the lentiviral vector particles.

Preferably, a vector (i.e. a recombinant transfer vector) of the invention is an expression vector comprising appropriate means for expression of the hook fusion protein and/or the target fusion protein in a host cell.

Various promoters may be used to drive high expression of the nucleic acid sequence encoding the hook fusion protein and/or the target fusion protein. The promoter may be a tissue-specific, ubiquitous, constitutive or inducible promoter. Preferred promoters are notably functional in T cells and/or NK cells, preferably human T cells and human NK cells. In particular, preferred promoters are able to drive high expression of the hook fusion protein and the target fusion protein (notably a CAR as previously defined) from lentivectors in T cells or NK cells, preferably human T cells or NK T cells. For example, a promoter according to the invention can be selected from phosphoglycerate kinase promoter (PGK), elongation factor-1 alpha (EF-1 alpha) promoter including the short form of said promoter (EFS), viral promoters such as cytomegalovirus (CMV) immediate early enhancer and promoter, retroviral 5' and 3' LTR promoters including hybrid LTR promoters, human ubiquitin promoter, MHC class I promoter, MHC class II promoter, and β2 microglobulin (β2ηη) promoter. The promoters are advantageously human promoters, i.e., promoters from human cells or human viruses. Typically, the promoter can be a spleen focus-forming virus promoter (SFPV). Human ubiquitin promoter, MHC class I promoter, MHC class II promoter, and β2 microglobulin (β2ηη) promoter are more particular preferred. Preferably, the MHC class I promoter is an HLA-A2 promoter, an HLA-B7 promoter, an HLA-Cw5 promoter, an HLA-F, or an HLA-E promoter. In some embodiments the promoter is not a CMV promoter/enhancer, or is not a dectin-2 or MHCII promoter. Such promoters are well-known in the art and their sequences are available in sequence data base.

In one embodiment of the present invention, the nucleic acid encoding the hook fusion protein and the target fusion protein are inserted into separate vectors.

In another embodiment, the nucleic acid encoding the hook fusion protein and the target fusion protein are inserted into the same vector.

When the vector system comprises more than one vector, typically two or more vectors, said vectors are typically of the same type (e.g.: a lentiviral vector). In the following sections the vector can also be intended as "the one or more vector" or "the vector system". Preferably the present invention encompasses a lentiviral vector system and notably a lentiviral particle system.

Each coding sequence (i.e. the nucleic acids encoding respectively the hook fusion protein and the target fusion protein) can be inserted in a separate expression cassette. Each expression cassette therefore comprises the coding sequence (open reading frame or ORF) functionally linked to the regulatory sequences which allow the expression of the corresponding protein (hook fusion protein and target fusion protein) in the host cell, such as in particular promoter, promoter/enhancer, initiation codon (ATG), codon stop, transcription termination signal.

Alternatively, the hook fusion protein and the target fusion protein may also be expressed from a unique expression cassette using an Internal Ribosome Entry Site (IRES), or a self-cleaving 2A peptide inserted between the two coding sequences to allow simultaneous expression.

Typically, nucleic acids encoding the hook fusion protein and the target fusion protein can be inserted in a single expression vector, said single vector comprising a bicistronic expression cassette. Vectors containing biscitronic expression cassette are well known in the art. Advantageously, bicistronic expression cassettes contain an Internal Ribosome Entry Site (IRES) that enables the expression of both fusion proteins from a single promoter. Suitable commercially available bicistronic vectors can include, but are not limited to plasmids of the pIRES (Clontech), pBud (Invitrogen) and Vitality (Stratagene) series. Preferably, the nucleic acid located upstream of the IRES sequence is operably-linked to a promoter. Preferably the nucleic acid encoding the hook fusion protein is inserted upstream of the IRES sequence and the nucleic acid encoding the target fusion protein is inserted downstream of said IRES sequence to ensure that enough the hook fusion protein will be sufficiently expressed to retain every target fusion protein. In some embodiments multicistronic expression vectors may be used wherein more than one, typically at least two, nucleic acids encoding each a distinct hook and at least one nucleic acid encoding a target fusion protein are inserted. For example such a vector may include a nucleic acid encoding a hook as described in the present invention and a nucleic acid encoding a hook as previously described in WO 201612623.

A self-cleaving 2A peptide can also be used in replacement of IRES. Such strategy is highly advantageous because of its small size and high cleavage and translation efficacy between nucleic acid sequences upstream and downstream of the 2A peptide. Suitable 2A peptide according to the invention are notably described in Kim J H, Lee S-R, Li L-H, et al. High Cleavage Efficiency of a 2A Peptide Derived from Porcine Teschovirus-1 in Human Cell Lines, Zebrafish and Mice. PLoS ONE. 2011; 6(4):e18556. 2A peptides can be selected from FMDV 2A (abbreviated herein as F2A); equine rhinitis A virus (ERAV) 2A (E2A); porcine teschovirus-1 2A (P2A) and Thoseaasigna virus 2A (T2A). P2A or T2A peptide is preferred. Although the use of a self-cleaving 2A peptide is generally recommended when a stoichiometric expression of the sequences located upstream and downstream of the 2A peptide, the inventors have found that it could still be used advantageously in the present "RUSH" context.

Typically, the invention encompasses a vector notably and expression vector comprising a nucleic acid encoding the hook fusion protein as previously defined which is inserted upstream of a 2A peptide sequence and a nucleic encoding a target fusion protein which is inserted downstream of the 2A peptide. In this configuration, the hook fusion protein comprises an amino-terminal ER retention signal such as an Ii retention signal as previously described. The invention also encompasses a vector notably and expression vector comprising a nucleic acid encoding the hook fusion protein as previously defined which is inserted downstream of a 2A peptide sequence and a nucleic acid encoding a target fusion protein which is inserted upstream of the 2A peptide sequence. In this second configuration, the hook fusion protein comprises a carboxy terminal ER retention signal such as a KXKXX (SEQ ID NO: 3) retention signal as previously described.

In the embodiment as above described the target fusion protein is preferably a CAR as previously defined.

The present invention also encompasses a viral particle system comprising a vector system as previously defined. Preferably, the viral particle is a lentiviral particle. Preferably the vector system is a lentiviral vector system. In one embodiment, the vector system comprises one vector encoding both the hook fusion protein and the target fusion protein. Thus a preferred viral particle system according to the invention comprises a lentiviral vector comprising a nucleic acid encoding the hook fusion protein and a nucleic acid sequence encoding a target fusion protein in association with viral proteins. The lentiviral vector is preferably an integrating vector.

Isolated Cells of the Invention

The invention encompasses isolated cells, particularly cells of the immune system, comprising vectors and notably a viral vector particle system encoding at least a hook fusion protein as previously described. Preferably the vector system and/or lentiviral particle system further comprise a nucleic acid sequence encoding a target fusion protein. Preferably, the cells are T cells or NK cells.

In one embodiment, the cell contains the vector and/or viral vector particle systems integrated into the cellular genome (stable expression). In another embodiment, the cell contains the vector transiently expressing the hook fusion protein and preferably also the target fusion protein. In one embodiment, the cell produces lentiviral vector particles encoding the hook fusion protein and preferably also the target fusion protein. Preferably the target fusion protein is a CAR.

In various embodiments, the invention encompasses a cell line, a population of cells, or a cell culture comprising vectors, notably viral vector particles, encoding the hook fusion protein and preferably also the target fusion protein.

Kit According to the Invention:

The present invention also relates to a kit comprising a nucleic acid comprising at least a nucleic acid system as above defined and comprising at least a nucleic acid sequence encoding a hook fusion protein of the invention. Preferably said nucleic acid system further comprises a nucleic acid sequence encoding a target fusion protein. Preferentially, said nucleic sequences are comprises in the same nucleic acid.

The kit of the invention may alternatively comprise a vector system, a viral particle system, or a host cell as previously defined. Preferably the kit comprises a vector encoding a hook fusion protein and its corresponding target fusion protein. Preferably the vector is a viral vector notably a lentiviral vector. In another advantageous embodiment, the kit comprises a viral vector particle system comprising a viral vector system according to the invention.

Preferably the hook fusion protein comprises a streptavidin sequence. Most preferably the streptavidin sequence is the streptavidin sequence as set forth in SEQ ID NO: 1 or 2. In another embodiment, the streptavidin sequence is a low affinity streptavidin sequence as previously described.

In a preferred embodiment wherein the hook fusion protein comprises a streptavidin sequence, the kit further comprises a specific ligand. When the streptavidin sequence is a low affinity streptavidin sequence the ligand is preferably biotin. When the streptavidin sequence is not a low affinity streptavidin sequence the ligand is advantageously a biotin mimetic molecule selected from ALiS.

Method and Use for Regulating the Intracellular Trafficking of a Target Protein in a Host Cell:

The present invention also encompasses a method, typically an in vitro method, for regulating the intracellular trafficking of a target protein in a host cell. As mentioned previously, said target protein is a fusion protein comprising a hook binding domain.

This method comprises the expression in said host cell of a vector system or a viral particle as previously described; wherein the hook fusion protein and the target fusion protein are capable of conditional interaction in the absence of a ligand for the hook core domain.

Preferably the vector system comprises one vector comprising at least a nucleic acid sequence encoding the hook fusion protein and at least a nucleic acid encoding the target fusion protein. Preferably also the vector is a viral vector, notably a lentiviral vector.

Preferably, when a viral particle according to the invention is expressed in a host cell, said viral particle comprises at least a nucleic acid sequence encoding the hook fusion protein and at least a nucleic acid encoding the target fusion protein. Typically the viral particle is a lentiviral particle.

Preferably in the method of the invention, the hook domain of the hook fusion protein comprises a streptavidin sequence as previously mentioned the hook-binding domain comprises a streptavidin-binding peptide. In such a configuration release of the target fusion protein is achieved upon addition of biotin, which reverses interaction of the streptavidin sequence with the streptavidin-binding peptide. The use of such configuration is advantageous as biotin is a vitamin known to be well tolerated by the organism even at high doses.

Typically, to achieve full reversibility of the trafficking, a low affinity streptavidin sequence, as previously described is used. Alternatively, when wild-type streptavidin sequences or variants thereof with high affinity for biotin are used, full reversibility may be achieved by using biotin mimetic compounds such artificial ligands of streptavidin (ALiS) (see Terai T et al., 2015 and 2017 previously mentioned) exhibits fast dissociation kinetics and excellent cell permeability allowing repeated reversible cycling of the target protein localization between the plasma membrane and the endoplasmic reticulum. Indeed in these both configurations (using low affinity streptavidin or ALiS) the target fusion protein can be retrieved from the cell membrane by simple wash-out of the biotin or ALiS thanks to the use of the new cytoplasmic "trans" hook as herein disclosed.

The present invention also relates to the use of a hook fusion protein, or a nucleic acid or a nucleic acid system, or a vector system or a viral particle or a host cell or a kit as herein described for "trans control" of the trafficking of a target fusion protein; wherein said target fusion protein is a membrane protein comprising a hook-binding domain.

Medical Uses of the Invention:

The present invention further relates to a hook fusion protein, or a nucleic acid or a nucleic acid system, or a vector system or a viral particle or a host cell or a kit as herein described as a medicament. In particular, the present invention relates to the use of a vector system, notably a viral vector system and in particular a lentiviral vector system as a medicament. Said vector system comprises a nucleic acid sequence encoding a hook fusion protein and a nucleic acid sequence encoding a target fusion protein, which is preferably a CAR. Preferably also the hook fusion protein has a hook domain comprising a streptavidin sequence.

As previously mentioned the present invention based on an innovative hook fusion protein design allows full control of the expression of a corresponding target fusion protein to the cell membrane. This innovation is of particular relevance when the target fusion protein is a cytotoxic protein, such as a chimeric antigen receptor, which cell exposure must therefore be timely controlled.

The invention can also be used in treatment protocols against tumors and cancers and especially could be used in protocols for immunotherapy or vaccination therapy against cancers and tumors.

Preferably the nucleic acid sequences as above mentioned are included in the same vector, notably in the same integrating viral vector, in particular in the same integrating lentiviral vector.

Alternatively, the nucleic acid sequences as defined above are present in two separate vectors, notably in two separate integrating viral vectors, in particular two separate integrating lentiviral vectors.

In a preferred embodiment, the invention relates to the viral vector as above mentioned or to a viral vector particle comprising said viral vector for use as a medicament. Said viral vector or viral vector particle can be used for example in a therapeutic composition or vaccines which are capable of inducing or contributing to the occurrence or improvement of an immunological reaction with the CAR encoded by the vector. The invention therefore also encompasses an immunogenic composition comprising a viral vector as previously defined.

The invention encompasses methods of administration of a viral vector (notably a lentiviral vector) to a human. Preferred modes of administration include reinfusion of the modified T cells, preferably intravenously or intra-articular administration, most preferably intra-tumoral administration.

In one embodiment, viral vector particles according to the invention can be administered to T or NK cells. The obtained modified T cells or NK cells can be further administered to a human.

The viral vector and viral vector particles according to the invention have the ability to redirect the specificity and function of T lymphocytes and/or other immune cells such as NK cells. They can rapidly generate T cells targeted to a specific tumor antigen or an antigen relevant in other pathologies like auto-immune diseases.

The viral vector and viral vector particles of the invention can therefore be used in methods of treatment and methods of inducing an immune response comprising administering the viral vector to a cell, preferably a T or NK cell, administering the cell to a host, and generating a specific immune response that redirects the specificity and function of T lymphocytes and/or other immune cells.

A particular advantage of the immunogenic compositions of the invention is that they can be used to redirect the specificity and function of T lymphocytes and other immune cells against multiple antigens against which the CAR in the vector or vector particles are directed. As a result, the invention encompasses a composition that could be used in therapeutic vaccination protocols. In particular, it can be used in combination with adjuvants, other immunogenic compositions, chemotherapy, or any other therapeutic treatment.

The method can further comprise administering biotin or a biotin mimetic as previously described to the human to release the target fusion protein and in particular the CAR from the ER Preferably, the biotin is administered at an initial concentration of at least, 0.2, 0.4, 0.8. 1.6, 3.2, 5, 10, 20, 40, or 80 µM.

Having thus described different embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein.

FIGURE LEGENDS

FIG. 1: Schematic representation of the bicistronic plasmid coding for the known (Cs-Ii), newly Hooks and reporter gene. The Hooks are (A) cytoplasmic hook (Str-Ii, streptavidin (str)) fused to the isoform of the human invariant chain of the major histocompatibility complex (Ii; a type II protein) containing an ER retention arginine-based motif at the N-terminal); (B) soluble Cytoplasmic Streptavidin with the endocytosis signal (YXXI (SEQ ID NO: 28), X any aa) and ER retention signal (KKXX (SEQ ID NO: 4), X any aa); (C) cytoplasmic mini Hook with a Ii retention signal in the N-terminal and the endocytosis signal in C-terminal. These gene are expressed under the control of the CMV promoter and separated by a synthetic intron, i.e. intervening sequence (IVS) followed by an internal ribosome entry site (IRES) (Boncompain, Divoux et al. 2012).

Figure 2:
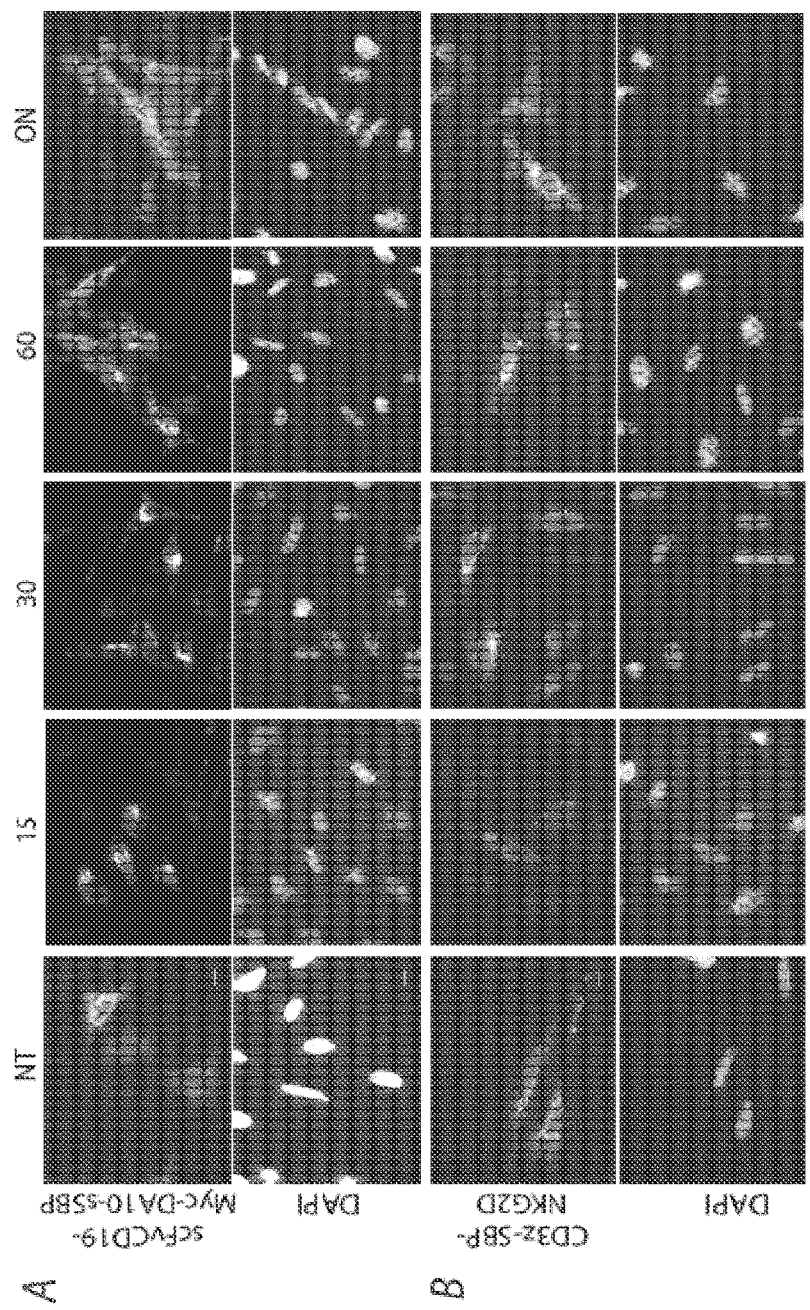

FIG. 2: Traffic of RUSH based constructs using the streptavidin containing an endocytosis signal and the ER retention signal KKXX (SEQ ID NO: 4) hook. HeLa cells expressing A) scFv (CD19)-myc-DAP10-sSBP reporter (anti-myc stained) or B) CD3-SBP-NKG2D co-transfected with myc-DAP10 (DAP10 is required for NKG2D traffic) (anti-NKG2D stained). The cells were non-treated (NT) and treated with biotin and different time points were recorded. Overnight treatment (ON) was performed by adding biotin immediately after adding transduction solution and it is representative of the protein steady state. Nucleus was stained using DAPI.

Figure 3:
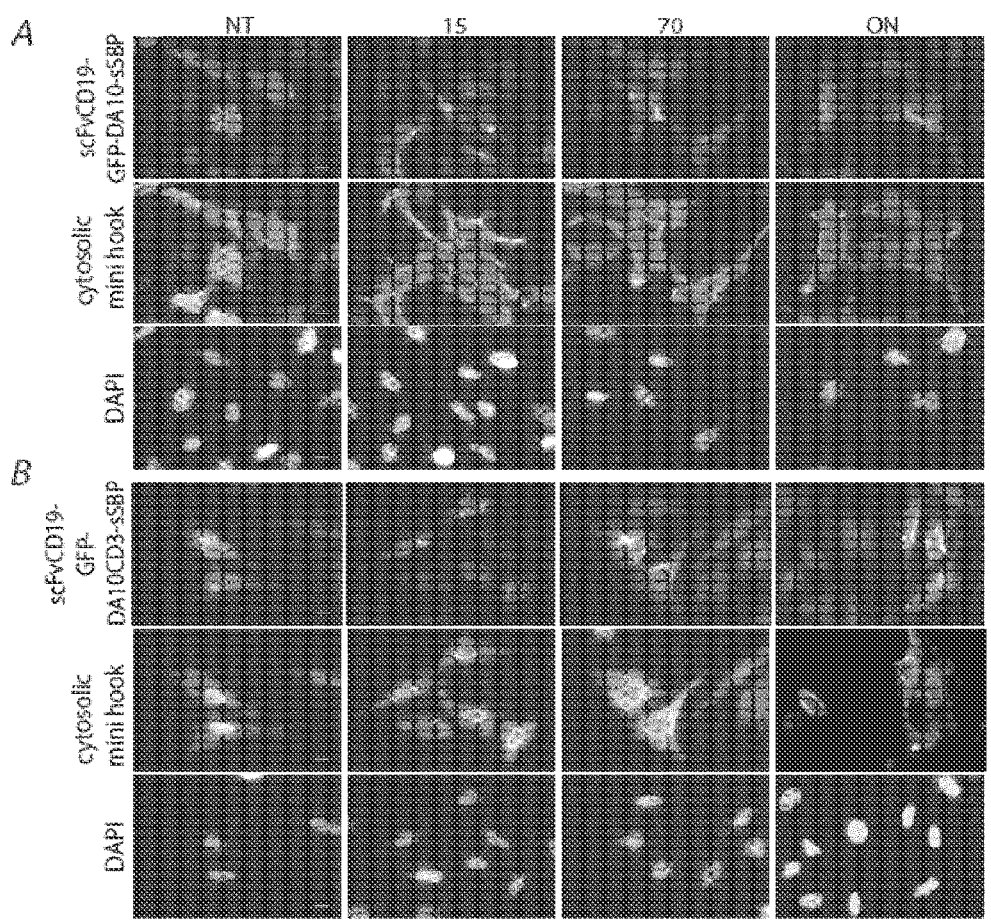

FIG. 3: Traffic of RUSH based constructs using the soluble mini hook containing an endocytosis signal. HeLa cells expressing A) scFv (CD19)-GFP-DAP10-sSBP reporter or B) scFv (CD19)-GFP-DAP10CD3-sSBP. Streptavidin in the mini hook was stained with anti-Str. The cells were non-treated (NT) and treated with biotin and different time points were recorded. Overnight treatment (ON) was performed by adding biotin immediately after adding transduction solution and it is representative of the protein steady state. Nucleus was stained using DAPI.

Figure 4:
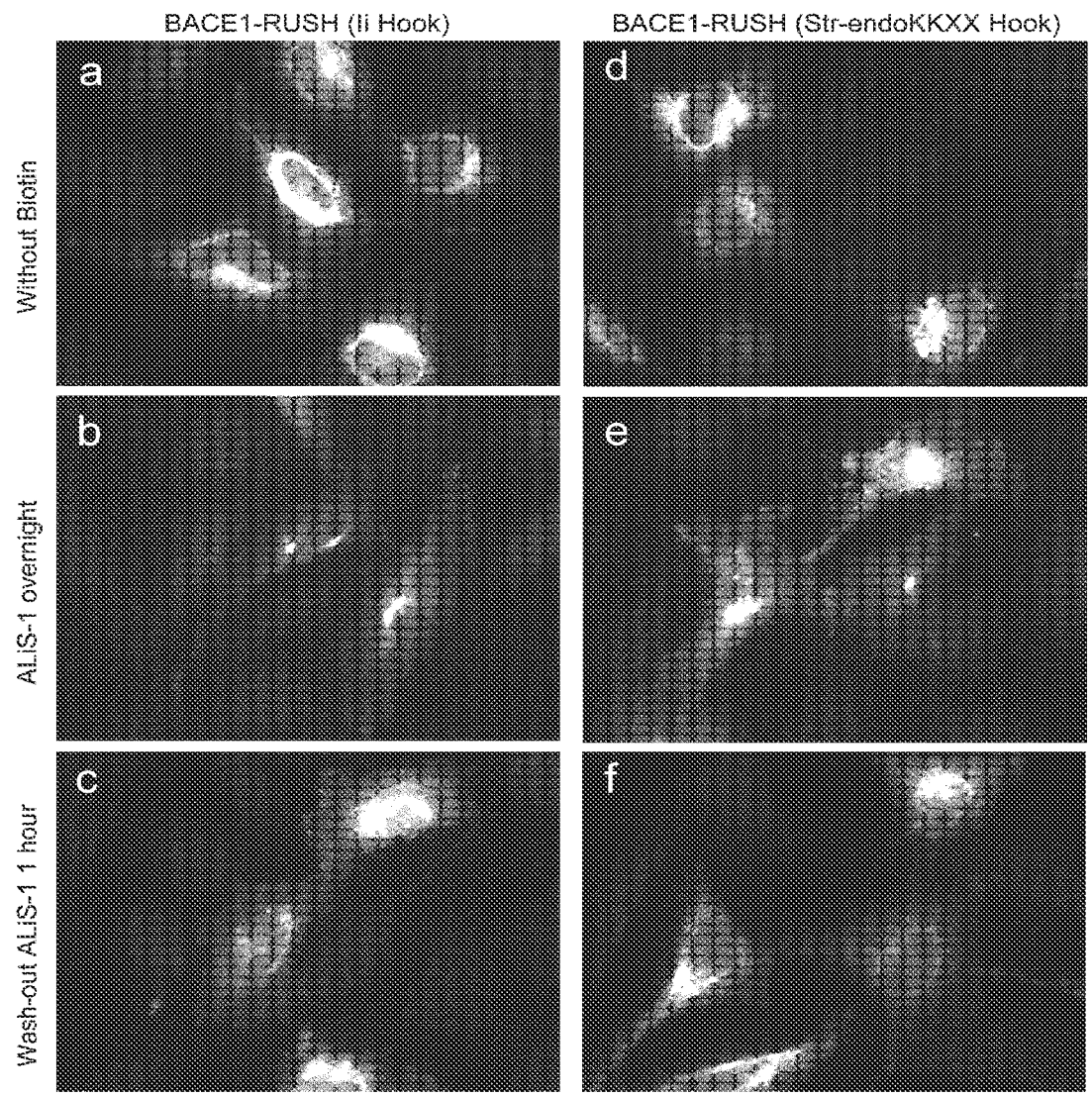

FIG. 4: The soluble Str-endoKKXX Hook allows retention at the level of the ER and retrieval from the cell surface. HeLa cells were transfected by BACE1-GFP-SBP (BACE1-RUSH) together with an Invariant chain-based Hook (Ii Hook,a-c) or a cytoplasmic Hook bearing both an ER transport signal and an endocytosis signal (Str-endoKKXX, d-f). Upon transfection in the absence of releasing molecule (without biotin, a,d), BACE1-RUSH is retained in the ER. Addition of the biotin-mimetic molecule ALiS-1 overnight (b, e) allows efficient release of BACE1-RUSH and its transport to the cell surface. Washing-out ALiS-1 for 1 hour (c,f) does not allow to capture cell surface localized BAC1-RUSH if transfected with the Ii-based Hook (c) while it is efficiently transported back to the ER when expressed with Str-endoKKXX highlighting the capacity of the new Hook to mediate transport form the plasma membrane to the ER in addition to its ability to retain proteins in the ER.

Figure 5:
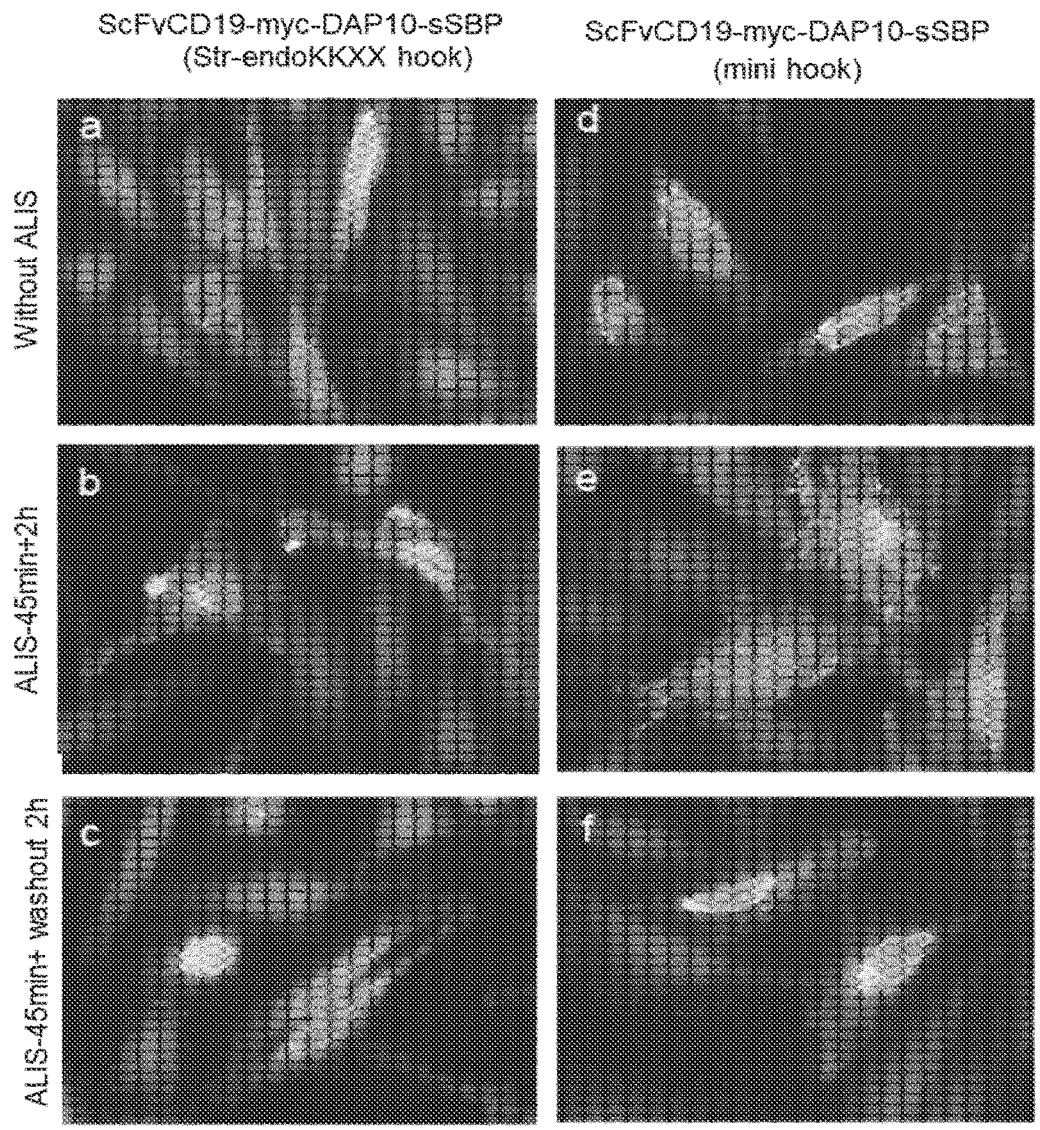

FIG. 5: The soluble miniIi Hook allows retention at the level of the ER and retrieval from the cell surface. HeLa cells were transfected by scFv (CD19)-myc-DAP10-sSBP together with a cytoplasmic Hook bearing both an ER transport signal and an endocytosis signal (Str-endoKKXX, a-c) or soluble mini hook containing an endocytosis signal (mini hook, d-f). Upon transfection in the absence of releasing molecule (without ALIS, a,d), scFv (CD19)-myc-DAP10-sSBP is retained in the ER. Addition of the biotin-mimetic molecule ALiS-1 45 min (b, e) allows efficient release of scFv (CD19)-myc-DAP10-sSBP and its transport to the cell surface. Washing-out ALiS-1 for 2 hours (c,f) efficiently transported back scFv (CD19)-myc-DAP10-sSBP to the ER when expressed with Str-endoKKXX or mini hook highlighting the capacity of the new Hooks to mediate transport form the plasma membrane to the ER in addition to its ability to retain proteins in the ER.

Figure 6:
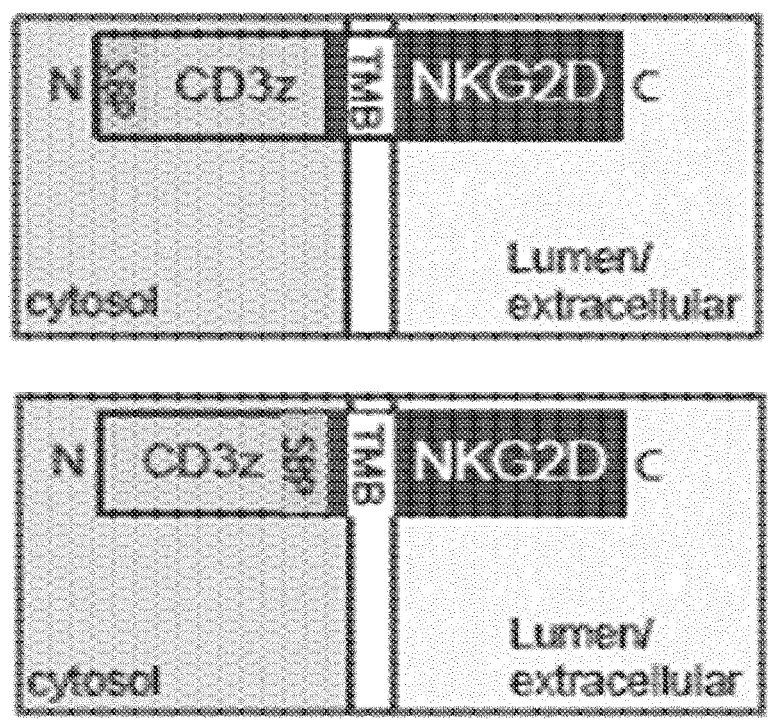

FIG. 6: Schematic representation of the NKG2D CAR. NKG2D (type II protein) is fused to CD3 zeta domain and to SBP in two distinct positions.

EXAMPLES

In the examples below, the term "Hook" refers to the hook fusion protein comprising the hook domain, and the term "Reporter" refers to the target membrane protein comprising the hook-binding domain.

Methods and Material

Constructs

FIG. 1 shows a schematic representation of the Hook constructs by Boncompain et al (FIG. 1A), and of the new hooks according to the present invention (FIG. 1B, 1C). Those are inserted in the bicistronic vector using multicloning sites and the reporter using the typical cloning cassettes of the previously published RUSH vector. The soluble streptavidin containing an endocytosis signal and the ER retention signal KKXX (SEQ ID NO: 4) were built by gene synthesis (gBlocks Gene Fragments—Integrated DNA Technologies or GeneArt/Thermo-Fisher). The soluble mini hook containing a endocytosis signal was synthetized by gene syntheses (gBlocks Gene Fragments—Integrated DNA Technologies) was generated by PCR amplification of the previously described luminal Ii-Str (Boncompain, Divoux et al. 2012), using the primers Fow-Nhe-IiMini-Str (5'-CTAgctagccATGCACAGAAGAAGAAGCAGAAGCg-accctagcaaagactcaaaagc-3')(SEQ ID NO:19) and Rev-mini-Ii-2nd-Xho (5'-CTCGAGgcggctgcacttgctctc-3')(SEQ ID NO: 20) for amplification of the 46 aa of Ii and for streptavidin amplification the primer Fow-Xho-Str (5'-CTCGAGGACCCTAGCAAAGACTCA-3')(SEQ ID NO: 21) and REV-Ires (5 '-GGATCAGTTATCTATGCG-3') (SEQ ID NO: 22). The fragments generated were digested with the respective enzymes and clone into the pCMV vector used previously in (Boncompain, Divoux et al. 2012). The sequences were evaluated and validate by sequencing. The several reporters were used tagged with a fluorescent protein (GFP). The sequence of some of the reporter were synthesized by gene syntheses (gBlocks Gene Fragments—Integrated DNA Technologies), other were previously generated in (Boncompain, Divoux et al. 2012).

Cell Culture and Transfection:

HeLa cells were cultivated at 37° C. and 5% of $CO_2$ in Dulbecco's modified Eagle medium (DMEM) supplemented with 10%1-BS (Biowest), 1 mM sodium Pyruvate and 100 µM of penicillin and streptomycin (Invitrogen). HeLa cells were transfected with the plasmid of interest using Calcium phosphate protocol in the presence of 25 mM of HEPES. Briefly, the plasmids coding the sequence of CAR based RUSH such as CD3-SBP-NKG2D (SEQ ID NO: 13), scFv (CD19)-GFP-DAP10CD3-sSBP (SEQ ID NO: 23), scFv (CD19)-GFP-DAP10-SBPdel (SEQ ID NO: 24), scFv (CD19)-mycDAP10-SBP (SEQ ID NO: 25) or BACE1-SBP-EGFP (SEQ ID NO: 26) (2.5 ug per 1 mL of final volume) were add to 1 mM tris-HCl pH 8.02 buffer followed by the addition of 10% of $CaCl_2$ and incubated for 5 min (RT). Then this mix was add drop by drop into 2× concentrate HEBS buffer (160 mM NaCl, 1.5 mM $Na_2HPO_4$, 50 mM Hepes PH 7.04-7.05) while vortexing. The cells were incubated with this solution overnight at 37° C. and 5% of $CO_2$.

Time Course Release Using Biotin:

The cells were seeded into a glass coverslips for fixed cell immunofluorescence and/or live imaging. In the next day the cells were transfected with the plasmids coding the construct of interest as previously described. For the steady state of the protein/construct, 40 μM final concentration of biotin was added (4 mM stock solution) just after addition of the transfection solution. The presence of biotin prevented the interaction of the reporter (target membrane protein) with the hook, allowing the normal traffic of the reporter. In the next day, the cells in the coverslips were incubated at different time point with a final concentration of 40 μM of biotin, allowing the traffic of the reporter and then prepared for immunofluorescence.

Biotin-mimetic molecule ALiS-1 was prepared in DMSO to 20 mM (stock solution) and the cells were treated with 40 μM final concentration to prevent the interaction between the reporter (target membrane protein) and the hook.

Immunofluorescence:

Cells coated in the coverslips were washed once in 1×PBS buffer, fixed in 3% of paraformaldehyde (PFA) (10-15 min, RT), washed (2×) and incubated with 50 mM of $NH_4Cl$ (5 min, RT) to quench free aldehydes. The cells were then permeabilized using a solution of PBS containing bovine serum Albumin (BSA, 0.5%, Sigma-Aldrich) and saponin (Sapo, 0.05% Sigma-Aldrich)(15 min, RT). When the protein was not fluorescent labelled, we used antibodies for their detection. These include the monoclonal anti human NKG2D (1/800, Biolegend), and anti-myc tag from mouse (1/2000, clone 9E10) or anti-myc from rabbit (1/500, Cell Signaling). The coverslip were mounted in Mowiol (Calbiochem) supplemented with DAPI (4',6-Diamidino-2-phenylindole) for DNA staining Results Soluble Streptavidin Containing an Endocytosis Signal and the ER Retention Signal KKXX (SEQ ID NO: 4):

The soluble streptavidin containing an endocytosis signal and the ER retention signal KKXX (SEQ ID NO: 4) was used to synchronized the traffic of the CAR, scFvCD19-Myc-DAP10-sSBP (sSBP; small streptavidin binding peptide, with 28 amino-acids (aa), instead of the typical 36 aa) (FIG. 2, A) and the NKG2D based CAR, with SBP into two different positions (FIG. 2, B). These include a SBP as CD3-SBP-NKG2D (FIG. 2, B). The NKG2D based CARs were always co-transfected with Myc-DAP10, since DAP10 is required for NKG2D traffic. The scFvCD19-Myc-DAP10-sSBP was well retain in the ER by this Hook and upon addition of biotin is released and 15 min later reached the Golgi apparatus (FIG. 2, A). 30 min later, part of the protein is localized in the cells surface although some remained in the Golgi and at 60 min the majority is at the cell surface (FIG. 2, A). Overnight with biotin allow the traffic of the protein to the cell surface, presumably as in its steady state (FIG. 2, A). The CD3-SBP-NKG2D (FIG. 2, B) were co-transfected with DAP10 for their traffic Similar to the previous CAR, CD3-SBP-NKG2D (FIG. 2, B) is retained in the ER by this Hook. The traffic behavior of the CD3-SBP-NKG2D is very similar to the scFvCD19-Myc-DAP10-sSBP (FIG. 2, B). At 15 min the CD3-SBP-NKG2D is localized in the Golgi apparatus, 30 min after it started to reach the cell surface and 60 min, the majority of the NKG2D is at the cell surface, although some is still retain in the Golgi (FIG. 2, B).

Cytoplasmic Mini Hook:

To the cytoplasmic mini hook an endocytosis signal was added or not in the C-terminal. The endocytosis signal is similar to the one used for the soluble streptavidin containing an endocytosis signal and the ER retention signal KKXX (SEQ ID NO: 4) (FIG. 3). This newly developed soluble mini hook is efficient to retain the CARs scFv (CD19)-GFP-DAP10-sSBP reporter (FIG. 3, A) or scFv (CD19)-GFP-DAP10CD3-sSBP (FIG. 3, B) in the endoplasmic reticulum. To the construct scFv (CD19)-GFP-DAP10-sSBP was fused a CD3 zeta domain (activation domain) after DAP10 that should increase the activation capacity of the CAR (scFv (CD19)-GFP-DAP10CD3-sSBP). The addition of the biotin leads to the release of the mentioned CARs and at 15 min they reached the Golgi apparatus and at 30 min at cell surface, although some still remain in the Golgi. At 60 min with biotin, the majority of the CARs are at the cell surface similar to the overnight treatment with biotin (FIG. 3). We also observed the scFv (CD19)-GFP-DAP10CD3-sSBP CAR at 60 min and ON in the presence of biotin, is still retained at the Golgi apparatus even when the majority reached the cells surface.

Cytoplasmic Mini Hook and Soluble Str-endoKKXX Hook Reversible Capacity:

We could observe that both cytoplasmic mini Hook and str-endoKKXX allow the retention and release using a biotin-mimetic molecule ALiS-1 (Terai et al, J. Am. Chem. Soc, 2015; 137(33):10464-7) (FIGS. 4 and 5). Washing-out ALiS-1 allows the retrieval from surface localized BACE1-RUSH and scFv (CD19)-myc-DAP10-sSBP back to the ER. These highlighting the capacity of the new Hooks to mediate a reversible transport from the plasma membrane to the ER while maintain their ability to retain and thus release proteins in the ER.

The invention claimed is:

1. A hook fusion protein comprising:
a hook domain which is a streptavidin; and
at least one cytoplasmic carboxy terminal endoplasmic reticulum (ER) retention signal or at least one cytoplasmic amino terminal endoplasmic reticulum (ER) retention signal, or a combination thereof;
wherein the hook fusion protein is a soluble protein that localizes in the cytoplasm, and wherein the hook fusion protein does not comprise a transmembrane domain.

2. The hook fusion protein according to claim 1, wherein the hook domain is a streptavidin of sequence SEQ ID: NO 1.

3. The hook fusion protein according to claim 1, wherein the cytoplasmic carboxy terminal endoplasmic reticulum (ER) retention signal is KXKXX (SEQ ID NO: 30), wherein each X is any amino acid, and the cytoplasmic amino terminal endoplasmic reticulum (ER) retention signal is a fragment of an isoform of a human invariant chain of major histocompatibility complex protein Ii.

4. The hook fusion protein according to claim 1, further comprising an endocytosis signal.

5. The hook fusion protein according to claim 1, further comprising an endocytosis signal consisting of YXXI (SEQ ID NO: 28) wherein X is any amino acid.

6. The hook fusion protein according to claim 1, consisting of:
a hook domain which is a streptavidin;
a cytoplasmic carboxy terminal endoplasmic reticulum (ER) retention signal or a cytoplasmic amino terminal endoplasmic reticulum (ER) retention signal, wherein the cytoplasmic carboxy terminal endoplasmic reticulum (ER) retention signal is KXKXX (SEQ ID NO: 30), wherein each X is any amino acid, and the amino terminal endoplasmic reticulum (ER) retention signal is a fragment of an isoform of a human invariant chain of major histocompatibility complex protein Ii; and
at least one endocytosis signal;
wherein the hook fusion protein is a soluble protein that localizes in the cytoplasm, and wherein the hook fusion protein does not comprise a transmembrane domain.

7. The hook fusion protein according to claim 1, wherein the hook domain is a low affinity streptavidin mutant sequence having at least 80% identity with SEQ ID NO: 1 or SEQ ID NO: 2.

8. The hook fusion protein according to claim 1, wherein the hook domain is a streptavidin having a monomeric form, a tetrameric form, or a core form.

9. The hook fusion protein according to claim 1, wherein the streptavidin is a streptavidin homolog consisting of avidin or rhizavidin.

* * * * *

SEQUENCE LISTING

```
Sequence total quantity: 30
SEQ ID NO: 1            moltype = AA  length = 160
FEATURE                 Location/Qualifiers
source                  1..160
                        mol_type = protein
                        organism = Streptomyces avidinii
SEQUENCE: 1
MDPSKDSKAQ VSAAEAGITG TWYNQLGSTF IVTAGADGAL TGTYESAVGN AESRYVLTGR   60
YDSAPATDGS GTALGWTVAW KNNYRNAHSA TTWSGQYVGG AEARINTQWL LTSGTTEANA  120
WKSTLVGHDT FTKVKPSAAS IDAAKKAGVN NGNPLDAVQQ                        160

SEQ ID NO: 2            moltype = AA  length = 160
FEATURE                 Location/Qualifiers
REGION                  1..160
                        note = monomeric streptavidin
source                  1..160
                        mol_type = protein
                        organism = synthetic construct
SEQUENCE: 2
MDPSKDSKAQ VSAAEAGITG TWYNQLGSTF IVTAGADGAL TGTYESAVGN AESRYTLTGR   60
```

```
YDSAPATDGS GTALGWRVAW KNNYRNAHSA TTWSGQYVGG AEARINTQWT LTSGTTEANA    120
WKSTLRGHDT FTKVKPSAAS IDAAKKAGVN NGNPLDAVQQ                          160

SEQ ID NO: 3             moltype =    length =
SEQUENCE: 3
000

SEQ ID NO: 4             moltype =    length =
SEQUENCE: 4
000

SEQ ID NO: 5             moltype = AA   length = 46
FEATURE                  Location/Qualifiers
REGION                   1..46
                         note = N ter retention sequence
source                   1..46
                         mol_type = protein
                         organism = synthetic construct
SEQUENCE: 5
MHRRRARACR EDQKPVTDDQ RDLISNNEQL PMLGRRPGAP ESKCSR                    46

SEQ ID NO: 6             moltype = DNA   length = 666
FEATURE                  Location/Qualifiers
misc_feature             1..666
                         note = nucleotide sequence coding for soluble cytoplasmic
                         hook having N terminal ER retention signal
source                   1..666
                         mol_type = other DNA
                         organism = synthetic construct
SEQUENCE: 6
atgcacagga ggagagccag ggcctgtcgg gaagatcaaa agccagtcac tgatgatcag     60
cgcgacctta tctccaacaa tgagcaactg cccatgctgg gccggcgcc tggggccccg    120
gagagcaagt gcagccgcgc tagcgaccct agcaaagact caaaagctca ggtgtccgct    180
gccgaggctg gcattactgg aacatggtac aatcagctcg ggagcacctt tattgtgact    240
gctggagccg atggagccct caccggaaca tacgaatctg ctgtgggaaa cgccgaatca    300
cggtacgtcc tcactggccg atacgatagt gcccctgcca ccgacggatc tgggactgcc    360
ctgggatgga ctgtcgcttg gaaaaacaac taccggaatg ctcattctgc cacaacatgg    420
agtggacagt acgtgggagg cgctgaggct agaatcaata cacagtggct gctcacatct    480
ggcacaaccg aggcaaatgc ttggaaatcc accctggtgg gacatgacac attcaccaaa    540
gtgaaaccct ccgccgcttc aattgatgcc gccaaaaaag ccggagtcaa caacggcaat    600
cctctggatg ccgtccagca gtaccctac gacgtgcccg actacgccgc cggctaccag    660
accatc                                                                666

SEQ ID NO: 7             moltype = DNA   length = 621
FEATURE                  Location/Qualifiers
misc_feature             1..621
                         note = nucleotide sequence coding for soluble cytoplasmic
                         hook having N ter ER retention signal
source                   1..621
                         mol_type = other DNA
                         organism = synthetic construct
SEQUENCE: 7
atgcacagga ggagagccag ggcctgtcgg gaagatcaaa agccagtcat cgatgatcag     60
cgcgacctta tctccaacaa tgagcaactg cccatgctgg gccggcgcc tggggccccg    120
gagagcaagt gcagccgcct cgaggaccct agcaaagact caaaagctca ggtgtccgct    180
gccgaggctg gcattactgg aacatggtac aatcagctcg ggagcacctt tattgtgact    240
gctggagccg atggagccct caccggaaca tacgaatctg ctgtgggaaa cgccgaatca    300
cggtacgtcc tcactggccg atacgatagt gcccctgcca ccgacggatc tgggactgcc    360
ctgggatgga ctgtcgcttg gaaaaacaac taccggaatg ctcattctgc cacaacatgg    420
agtggacagt acgtgggagg cgctgaggct agaatcaata cacagtggct gctcacatct    480
ggcacaaccg aggcaaatgc ttggaaatcc accctggtgg gacatgacac attcaccaaa    540
gtgaaaccct ccgccgcttc aatcgatgcc gccaaaaaag ccggagtcaa caacggcaat    600
cctctggatg ccgtccagca g                                               621

SEQ ID NO: 8             moltype = DNA   length = 546
FEATURE                  Location/Qualifiers
misc_feature             1..546
                         note = nucleotide sequence coding for soluble cytoplasmic
                         hook having C ter ER retention sequence
source                   1..546
                         mol_type = other DNA
                         organism = synthetic construct
SEQUENCE: 8
atggacccca gcaaggacag caaggcccag gtgagcgccg ccgaggccgg catcaccggc     60
acctggtaca accagctggg cagcaccttc atcgtgaccg ccggcgccga cggcgccctg    120
accggcacct acgagagcgc cgtgggcaac gccgagagca gatacgtgct gaccggcaga    180
tacgacagcg cccccgccac cgacggcagc ggcaccgccc tgggctggac cgtggcctgg    240
aagaacaact acagaaacgc ccacagcgcc accacctgga gcggcagta cgtgggcggc    300
gccgaggcca gaatcaacac ccagtggctg ctgaccagcg gcaccaccga ggccaacgcc    360
```

```
tggaagagca      ccctggtggg      ccacgacacc      ttcaccaagg      tgaagcccag      cgccgccagc      420
atcgacgccg      ccaagaaggc      cggcgtgaac      aacggcaacc      ccctggacgc      cgtgcagcag      480
ggcggatcct      acccctacga      cgtgcccgac      tacgccgccg      gctaccagac      catcaagaag      540
accaac                                                                                          546

SEQ ID NO: 9              moltype = AA   length = 38
FEATURE                   Location/Qualifiers
REGION                    1..38
                          note = SBP
source                    1..38
                          mol_type = protein
                          organism = synthetic construct
SEQUENCE: 9
MDEKTTGWRG GHVVEGLAGE LEQLRARLEH HPQGQREP                                        38

SEQ ID NO: 10             moltype = DNA   length = 114
FEATURE                   Location/Qualifiers
misc_feature              1..114
                          note = SBP nucleotide sequence
source                    1..114
                          mol_type = other DNA
                          organism = synthetic construct
SEQUENCE: 10
atggacgaga      aaaccaccgg      ctggcgggga      ggccacgtgg      tggaaggact      ggccggcgag      60
ctggaacagc      tgcgggccag      actggaacac      caccccagg       gccagagaga      gccc            114

SEQ ID NO: 11             moltype = AA   length = 28
FEATURE                   Location/Qualifiers
REGION                    1..28
                          note = short SBP
source                    1..28
                          mol_type = protein
                          organism = synthetic construct
SEQUENCE: 11
GHVVEGLAGE LEQLRARLEH HPQGQREP                                                   28

SEQ ID NO: 12             moltype = AA   length = 29
FEATURE                   Location/Qualifiers
REGION                    1..29
                          note = short SBP variant
source                    1..29
                          mol_type = protein
                          organism = synthetic construct
SEQUENCE: 12
GGHVVEGLAG ELEQLRARLE HHPQGQREP                                                  29

SEQ ID NO: 13             moltype = DNA   length = 1137
FEATURE                   Location/Qualifiers
misc_feature              1..1137
                          note = CAR nucleotide sequence
source                    1..1137
                          mol_type = other DNA
                          organism = synthetic construct
SEQUENCE: 13
atgagagtga      agttcagcag      gagcgcagac      gcccccgcgt      accagcaggg      ccagaaccag      60
ctctataacg      agctcaatct      aggacgaaga      gaggagtacg      atgttttgga      caagagacgt      120
ggccgggacc      ctgagatggg      gggaaagccg      cagagaagga      gaaccctca       ggaaggcctg      180
tacaatgaac      tgcagaaaga      taagatggcg      gaggcctaca      gtgagattgg      gatgaaaggc      240
gagcgccgga      ggggcaaggg      gcacgatggc      ctttaccagg      gtctcagtac      agccaccaga      300
gacacctacg      acgcccttca      catgcaggcc      ctgccccctc      gcgaattccc      tgcaggaggc      360
cggccagacg      agaagaccac      cggctggaga      ggcggccacg      tggtggaggg      cctggccggc      420
gagctggagc      agctgagagc      cagactggag      caccacccc       agggcagag       agagcccagc      480
gatcgcgggt      ggattcgtgg      tcggaggtct      cgacacagct      gggagatgag      tgaatttcat      540
aattataact      tggatctgaa      gaagagtgat      ttttcaacac      gatggcaaaa      gcaaagatgt      600
ccagtagtca      aaagcaaatg      tagagaaaat      gcatctccat      tttttttctg      ctgcttcatc      660
gctgtagcca      tgggaatccg      tttcattatt      atggtagcaa      tatggagtgc      tgtattccta      720
aactcattat      tcaaccaaga      agttcaaatt      cccttgaccg      aaagttactg      tgggccatgt      780
cctaaaaact      ggatatgtta      caaaaataac      tgctaccaat      tttttgatga      gagtaaaaac      840
tggtatgaa       gccaggcttc      ttgtatgtct      caaaatgcca      gccttctgaa      agtatacagc      900
aaagaggacc      aggattttact     taaactggtg      aagtctatatc     attggatggg      actagtacac     960
attccaacaa      atggatcttg      gcagtgggaa      gatggctcca      ttctctcacc      caacctacta     1020
acaataattg      aaatgcagaa      gggagactgt      gcactctatg      catcgagctt      taaaggctat     1080
atagaaaact      gttcaactcc      aaatacatac      atctgcatgc      aaaggactgt      gtaatta        1137

SEQ ID NO: 14             moltype = AA   length = 46
FEATURE                   Location/Qualifiers
REGION                    1..46
                          note = N ter ER retention sequence
source                    1..46
```

```
                        mol_type = protein
                        organism = synthetic construct
SEQUENCE: 14
MHRRRARACR EDQKPVIDDQ RDLISNNEQL PMLGRRPGAP ESKCSR                   46

SEQ ID NO: 15           moltype =   length =
SEQUENCE: 15
000

SEQ ID NO: 16           moltype =   length =
SEQUENCE: 16
000

SEQ ID NO: 17           moltype =   length =
SEQUENCE: 17
000

SEQ ID NO: 18           moltype =   length =
SEQUENCE: 18
000

SEQ ID NO: 19           moltype = DNA   length = 57
FEATURE                 Location/Qualifiers
misc_feature            1..57
                        note = primer Forward-Nhe-IiMini-Str
source                  1..57
                        mol_type = other DNA
                        organism = synthetic construct
SEQUENCE: 19
ctagctagcc atgcacagaa gaagaagcag aagcgaccct agcaaagact caaaagc      57

SEQ ID NO: 20           moltype = DNA   length = 24
FEATURE                 Location/Qualifiers
misc_feature            1..24
                        note = Primer Reverse-mini-Ii-2nd-Xho
source                  1..24
                        mol_type = other DNA
                        organism = synthetic construct
SEQUENCE: 20
ctcgaggcgg ctgcacttgc tctc                                          24

SEQ ID NO: 21           moltype = DNA   length = 24
FEATURE                 Location/Qualifiers
misc_feature            1..24
                        note = primer Fow-Xho-Str
source                  1..24
                        mol_type = other DNA
                        organism = synthetic construct
SEQUENCE: 21
ctcgaggacc ctagcaaaga ctca                                          24

SEQ ID NO: 22           moltype = DNA   length = 18
FEATURE                 Location/Qualifiers
misc_feature            1..18
                        note = Primer REV-Ires
source                  1..18
                        mol_type = other DNA
                        organism = synthetic construct
SEQUENCE: 22
ggatcagtta tctatgcg                                                 18

SEQ ID NO: 23           moltype = DNA   length = 2187
FEATURE                 Location/Qualifiers
misc_feature            1..2187
                        note = scFvCD19-GFP-DAP10CD3z-SBPd-
source                  1..2187
                        mol_type = other DNA
                        organism = synthetic construct
SEQUENCE: 23
atggccttac cagtgaccgc cttgctcctg ccgctggcct tgctgctcca cgccgccagg   60
ccggatatcc agatgacaca gactacatcc tccctgtctg cctctctggg agacagagtc  120
accatcagtt gcagggcaag tcaggacatt agtaaatatt taaattggta tcagcagaaa  180
ccagatggaa ctgttaaact cctgatctac catacatcaa gattacactc aggagtccca  240
tcaaggttca gtggcagtgg gtctggaaca gattattctc tcaccattag caacctggag  300
caagaagata ttgccactta cttttgccaa cagggtaata cgcttccgta cacgttcgga  360
ggggggacca agctggagat cacaggtggc ggtggctcgg gcggtggtgg gtcgggtggc  420
ggcggatctg aggtgaaact gcaggagtca ggacctggcc tggtggcgcc ctcacagagc  480
ctgtccgtca catgcactgt ctcaggggtc tcattacccg actatggtgt aagctggatt  540
cgccagcctc cacgaaaggg tctggagtgg ctggagtaa  tatgggg tag tgaaaccaca  600
```

```
tactataatt cagctctcaa atccagactg accatcatca aggacaactc caagagccaa   660
gttttcttaa aaatgaacag tctgcaaact gatgacacag ccatttacta ctgtgccaaa   720
cattattact acggtggtag ctatgctatg gactactggg gccaaggaac ctcagtcacc   780
gtctcctcac ctgcaggtat ggtgagcaag ggcgaggagc tgttcaccgg ggtggtgccc   840
atcctggtcg agctggacgg cgacgtaaac ggccacaagt tcagcgtgtc cggcgagggc   900
gagggcgatg ccacctacgg caagctgacc ctgaagttca tctgcaccac cggcaagctg   960
cccgtgccct ggcccaccct cgtgaccacc ctgacctacg gcgtgcagtg cttcagccgc  1020
taccccgacc acatgaagca gcacgacttc ttcaagtccg ccatgcccga aggctacgtc  1080
caggagcgca ccatcttctt caaggacgac ggcaactaca agacccgcgc cgaggtgaag  1140
ttcgagggcg acaccctggt gaaccgcatc gagctgaagg gcatcgactt caaggaggac  1200
ggcaacatcc tggggcacaa gctggagtac aactacaaca gccacaacgt ctatatcatg  1260
gccgacaagc agaagaacgg catcaaggtg aacttcaaga tccgccacaa catcgaggac  1320
ggcagcgtgc agctcgccga ccactaccag cagaacaccc ccatcggcga cggccccgtg  1380
ctgctgcccg acaaccacta cctgagcacc cagtccgccc tgagcaaaga ccccaacgaa  1440
aagcgcgatc acatggtcct gctggagttc gtgaccgccg ccgggatcac tctcggcatg  1500
gacgagctgt acaagggccg gccacagacg actccaggag agatcatc actccctgcc  1560
ttttaccctg gcacttcagg ctcttgttcc ggatgtgggt ccctctctct gccgctcctg  1620
gcaggcctcg tggctgctga tgcggtggca tcgctgctca tcgtggggga ggtgttcctg  1680
tgcgcacgcc cacgccgcag ccccgcccaa gaagatggca aagtctacat caacatgcca  1740
ggcaggggcc ttaagagagt gaagttcagc aggagcgcag acgcccccgc gtaccagcag  1800
ggccagaacc agctctataa cgagctcaat ctaggacgaa gagaggagta cgatgttttg  1860
gacaagagac gtggccggga ccctgagatg ggggaaggc tgcagagaag gaagaaccct  1920
caggaaggcc tgtacaatga actgcagaaa gataagatgg cggaggccta cagtgagatt  1980
gggatgaaag gcgagcgccg gaggggcaag ggcacgatgc cctttaccca gggtctcagt  2040
acagccacca aggacaccta cgacgccctt cacatgcagg ccctgccccc tcgcaccggt  2100
ggccacgttg ttgaaggact ggctggggaa cttgaacaac ttcgtgcacg actggagcat  2160
cacccacaag gtcaacgtga accatga                                       2187

SEQ ID NO: 24            moltype = DNA   length = 1833
FEATURE                  Location/Qualifiers
misc_feature             1..1833
                         note = scFvCD19-GFP-DAP10-SBPdel
source                   1..1833
                         mol_type = other DNA
                         organism = synthetic construct
SEQUENCE: 24
atggccttac cagtgaccgc cttgctcctg ccgctggcct tgctgctcca cgccgccagg    60
ccggatatcc agatgacaca gactacatcc tccctgtctg cctctctggg agacagagtc   120
accatcagtt gcagggcaag tcaggacatt agtaaaatt taaattggta tcagcagaaa   180
ccagatggaa ctgttaaact cctgatctac catacatcaa gattacactc aggagtccca   240
tcaaggttca gtggcagtgg gtctggaaca gattattctc tcaccattag caacctggag   300
caagaagata ttgccactta ctttttgccaa cagggtaata cgcttccgta cacgttcgga   360
gggggacca agctggagat cacaggtggc ggtggctcgg gcggtggtgg gtcgggtggc   420
ggcggatctg aggtgaaact gcaggagtca ggacctggcc tggtggcgcc ctcacagagc   480
ctgtccgtca catgcactgt ctcaggggtc tcattacccg actatggtgt aagctggatt   540
cgccagcctc cacgaaaggg tctggagtgg ctgggagtaa tatgggggtag tgaaaccaca   600
tactataatt cagctctcaa atccagactg accatcatca aggacaactc caagagccaa   660
gttttcttaa aaatgaacag tctgcaaact gatgacacag ccatttacta ctgtgccaaa   720
cattattact acggtggtag ctatgctatg gactactggg gccaaggaac ctcagtcacc   780
gtctcctcac ctgcaggtat ggtgagcaag ggcgaggagc tgttcaccgg ggtggtgccc   840
atcctggtcg agctggacgg cgacgtaaac ggccacaagt tcagcgtgtc cggcgagggc   900
gagggcgatg ccacctacgg caagctgacc ctgaagttca tctgcaccac cggcaagctg   960
cccgtgccct ggcccaccct cgtgaccacc ctgacctacg gcgtgcagtg cttcagccgc  1020
taccccgacc acatgaagca gcacgacttc ttcaagtccg ccatgcccga aggctacgtc  1080
caggagcgca ccatcttctt caaggacgac ggcaactaca agacccgcgc cgaggtgaag  1140
ttcgagggcg acaccctggt gaaccgcatc gagctgaagg gcatcgactt caaggaggac  1200
ggcaacatcc tggggcacaa gctggagtac aactacaaca gccacaacgt ctatatcatg  1260
gccgacaagc agaagaacgg catcaaggtg aacttcaaga tccgccacaa catcgaggac  1320
ggcagcgtgc agctcgccga ccactaccag cagaacaccc ccatcggcga cggccccgtg  1380
ctgctgcccg acaaccacta cctgagcacc cagtccgccc tgagcaaaga ccccaacgaa  1440
aagcgcgatc acatggtcct gctggagttc gtgaccgccg ccgggatcac tctcggcatg  1500
gacgagctgt acaagggccg gccacagacg actccaggag agatcatc actccctgcc  1560
ttttaccctg gcacttcagg ctcttgttcc ggatgtgggt ccctctctct gccgctcctg  1620
gcaggcctcg tggctgctga tgcggtggca tcgctgctca tcgtggggga ggtgttcctg  1680
tgcgcacgcc cacgccgcag ccccgcccaa gaagatggca aagtctacat caacatgcca  1740
ggcaggggcc acgttgttga aggactggct ggggaacttg aacaacttcg tgcacgactg  1800
gagcatcacc cacaaggtca acgtgaacca tga                                1833

SEQ ID NO: 25            moltype = DNA   length = 1120
FEATURE                  Location/Qualifiers
misc_feature             1..1120
                         note = scFvCD19-mycDAP10SBP
source                   1..1120
                         mol_type = other DNA
                         organism = synthetic construct
SEQUENCE: 25
atggccttac cagtgaccgc cttgctcctg ccgctggcct tgctgctcca cgccgccagg    60
ccggatatcc agatgacaca gactacatcc tccctgtctg cctctctggg agacagagtc   120
accatcagtt gcagggcaag tcaggacatt agtaaaatt taaattggta tcagcagaaa   180
```

```
ccagatggaa ctgttaaact cctgatctac catacatcaa gattacactc aggagtccca   240
tcaaggttca gtggcagtgg gtctggaaca gattattctc tcaccattag caacctggag   300
caagaagata ttgccactta cttttgccaa caggtaata cgcttccgta cacgttcgga    360
gggggggacca agctggagat cacaggtggc ggtggctcgg gcggtggtgg gtcgggtggc  420
ggcggatctg aggtgaaact gcaggagtca ggacctggcc tggtggcgcc ctcacagagc   480
ctgtccgtca catgcactgt ctcagggtc tcattacccg actatggtgt aagctggatt    540
cgccagcctc cacgaaaggg tctgagtgg ctgggagtaa tatgggtag tgaaaccaca     600
tactataatt cagctctcaa atccagactg accatcatca aggacaactc caagagccaa   660
gttttcttaa aaatgaacag tctgcaaact gatgacacag ccatttacta ctgtgccaaa   720
cattattact acggtggtag ctatgctatg gactactggg gccaaggaac ctcagtcacc   780
gtctcctcac ctgcaggaga gcagaagctg atctcagagg aggacctggg ccggccacag   840
acgactccag gagagagatc atcactccct gccttttacc ctggcacttc aggctcttgt   900
tccggatgtg ggtccctctc tctgccgctc ctggcaggcc tcgtggctgc tgatgcggtg   960
gcatcgctgc tcatcgtggg ggcggtgttc ctgtgcgcac gcccacgccg cagccccgcc  1020
caagaagatg gcaaagtcta catcaacatg ccaggcaggg gccacgttgt tgaaggactg  1080
gctggggaac ttgaacaact tcgtgcacga ctggagcatc                        1120

SEQ ID NO: 26          moltype = DNA  length = 2295
FEATURE                Location/Qualifiers
misc_feature           1..2295
                       note = BACE1-SBP-EGFP
source                 1..2295
                       mol_type = other DNA
                       organism = synthetic construct SEQUENCE: 26
atgggcccaag ccctgccctg gctcctgctg tggatgggcg cgggagtgct gcctgcccac    60
ggcacccagc acggcatccg gctgcccctg cgcagcggcc tgggggggcgc ccccctgggg  120
ctgcggctgc cccgggagac cgacgaagag cccgaggagc ccggccggag ggcagcttt    180
gtggagatgt ggacaacct gaggggcaag tcggggcagg gctactacgt ggagatgacc    240
gtgggcagcc cccgcagac ccccaacatc ctggttggata caggcagcag taactttgca   300
gtgggtgctg ccccccaccc cttcctgcat cgctactacc agaggcagct gtccagcaca   360
taccgggacc tccggaaggg tgtgtatgt ccctacaccc agggcaagtg ggaaggggag    420
ctgggcaccg acctggtaag catccccccat ggccccaacg tcactgtgcg tgccaacatt  480
gctgccatca ctgaatcaga caagttcttc atcaacggct gcaactggga aggcatccg    540
gggctggcct atgctgagat tgcccaggcct gacgactccc tggagccttt ctttgactct  600
ctggtaaagc agacccacgt tcccaaacctc ttctccctgc agctttgtgg tgctggcttc  660
ccccctcaacc agtctgaagt gctggcctct gtcggaggga gcatgatcat tggaggtatc  720
gaccactcgc tgtacacagg cagtctctgg tatacaccca tccggcggga gtggtattat   780
gaggtgatca ttgtgcgggt ggagatcaat ggacaggatc tgaaaatgga ctgcaaggag   840
tacaactatg acaagagcat tgtggacagt ggcaccacca accttcgttt gcccaagaaa   900
gtgtttgaag ctgcagtcaa atccatcaag gcagcctcct ccacgagaa gttccctgat    960
ggtttctggc taggagagca gctggtgtgc tggcaagcag gcaccacccc ttggaacatt  1020
tcccagtca tctcactcta cctaatgggt gaggttacca acagtcctc catcatcacc    1080
atccttccgc agcaatacct gcggccagtg gaagatgtgg ccacgtccca agacgactgt  1140
tacaagtttg ccatctcaca gtcatccacg gcactgttta gggagctgt tatcatggag   1200
ggcttctacg ttgtctttga tcgggcccga aaacgaattg gcttcgctgt cagcgcttgc   1260
catgtgcacg atgagttcag gacggcagcg gtggaagggcc ttttgtcac cttggacatg  1320
gaagactgtg gctacaacat tccacagaca gatgagtcaa ccctcatgac catagcctat   1380
gtcatggctg ccatctgcgc cctcttcatg ctgccactct gcctcatggt gtgtaggaat  1440
tccatggacg agaagaccac tggttggcga ggtggacacg ttgttgaagg actggctggg  1500
gaacttgaac aacttcgtgc acgactggag catcacccac aaggtcaacg tgaaccatct  1560
gcaggtatgg tgagcaaggg cgaggagctg ttcaccgggg tggtgcccat cctggtcgag  1620
ctggacggcg acgtaaacgg ccacaagttc agctgtccg gcgagggcga gggcgatgcc   1680
acctacggca agctgaccct gaagttcatc tgcaccaccg gcaagctgcc cgtgccctgg  1740
cccaccctcg tgaccaccct gacctacggc gtgcagtgct tcagccgcta ccccgaccac  1800
atgaagcagc acgacttctt caagtccgcc atgcccgaag gctacgtcca ggagcgcacc  1860
atcttcttca aggacgacgg caactacaag acccgcgccg aggtgaagtt cgagggcgac  1920
accctggtga accgcatcga gctgaagggc atcgacttca aggaggacgg caacatcctg  1980
gggcacaagc tggagtacaa ctacaacagc cacaacgtct atatcatggc cgacaagcag  2040
aagaacggca tcaaggtgaa cttcaagatc cgccacaaca tcgaggacgg cagcgtgcag  2100
ctcgccgacc actaccagca gaacacccc atcggcgacg gccccgtgct gctgcccgac  2160
aaccactacc tgagcaccca gtccgccctg agcaaagacc ccaacgagaa gcgcgatcac  2220
atggtcctgc tggagttcgt gaccgccgcc gggatcactc tcggcatgga cgagctgtac  2280
aagggccggc cttaa                                                    2295

SEQ ID NO: 27          moltype = AA  length = 4
FEATURE                Location/Qualifiers
REGION                 1..4
                       note = ER retention signal
source                 1..4
                       mol_type = protein
                       organism = synthetic construct SEQUENCE: 27
KDEL                                                                   4

SEQ ID NO: 28          moltype =   length =
SEQUENCE: 28
000
```

| SEQ ID NO: 29 | moltype = | length = |
| SEQUENCE: 29 | | |
| 000 | | |

| SEQ ID NO: 30 | moltype = | length = |
| SEQUENCE: 30 | | |
| 000 | | |